United States Patent
Laughlin

(10) Patent No.: US 7,247,631 B2
(45) Date of Patent: *Jul. 24, 2007

(54) PEGYLATED INTERFERON ALFA-CCR5 ANTAGONIST COMBINATION HIV THERAPY

(75) Inventor: Mark A. Laughlin, Edison, NJ (US)

(73) Assignee: Schering Corporation, Kenilworth, NJ (US)

( * ) Notice: Subject to any disclaimer, the term of this patent is extended or adjusted under 35 U.S.C. 154(b) by 518 days.

This patent is subject to a terminal disclaimer.

(21) Appl. No.: 10/430,370

(22) Filed: May 6, 2003

(65) Prior Publication Data

US 2004/0076609 A1 Apr. 22, 2004

Related U.S. Application Data

(63) Continuation of application No. 09/562,729, filed on May 1, 2000, now Pat. No. 6,635,646.

(60) Provisional application No. 60/132,495, filed on May 4, 1999.

(51) Int. Cl.
*A61K 31/50* (2006.01)
*A61K 31/501* (2006.01)
*A61K 31/497* (2006.01)
*A01N 43/40* (2006.01)

(52) U.S. Cl. ............... 514/252.01; 514/253.01; 514/253.1; 514/253.11; 514/253.09; 514/340

(58) Field of Classification Search ......... 514/253.1, 514/253.11, 252.01, 340, 253.09, 253.01
See application file for complete search history.

(56) References Cited

U.S. PATENT DOCUMENTS 6,177,074 B1 1/2001 Glue et al. .............. 424/85.7
6,635,646 B1 * 10/2003 Laughlin ............... 514/252.11

FOREIGN PATENT DOCUMENTS

| WO | WO 97/42969 | 11/1997 |
| WO | WO 98/01425 | 1/1998 |
| WO | WO 98/06697 | 2/1998 |
| WO | WO 98/25617 | 6/1998 |
| WO | WO 98/48840 | 11/1998 |
| WO | WO 99/17773 | 4/1999 |
| WO | WO 00/00488 | 1/2000 |

OTHER PUBLICATIONS

Carpenter, C., et al Report of the NIH Panel to Define Principles of Therapy of HIV Infection, Ann. Intern Med. (vol. 128, No. 12 (part 2) pp. 1057-1078(1998).
Fauci, A., et a., Guidelines for the Use of Antiretroviral Agents in HIV-Infected Adults and Adolescents, Ann. Intern. Med. vol. 128(No. 12, Part 2) pp. 1079-1100 (1998).

* cited by examiner

*Primary Examiner*—San-ming Hui
(74) *Attorney, Agent, or Firm*—Melodie W. Henderson

(57) ABSTRACT

Methods for treating treatment-naive as well as treatment-experienced adult and pediatric patients having HIV-1 infections as well as patients co-infected with HIV-1 and HCV involving administering a therapeutically effective amount of pegylated interferon-alfa, e.g., pegylated interferon alfa-2*b*, in association with a therapeutically effective amount of a CCR5 antagonist or preferably further in association with a therapeutically effective amount of at least one of ribavirin, IL-2, IL-12, pentafuside alone or in combination with a therapeutically effective amount of an anti-HIV-1 drug therapy, e.g., HAART are disclosed.

10 Claims, No Drawings

PEGYLATED INTERFERON ALFA-CCR5 ANTAGONIST COMBINATION HIV THERAPY

CROSS-REFERENCE TO RELATED APPLICATIONS

This application is (1) a continuation application of U.S. patent application Ser. No. 09/562,729, filed May 1, 2000, now U.S. Pat. No. 6,635,646 now allowed, which claims benefit of U.S. Provisional Application Ser. No. 60/132,495, filed May 4, 1999, now abandoned, and (2) related to commonly-owned U.S. patent application Ser. No. 09/562,814, now U.S. Pat. No. 6,391,865; and (3) related to commonly-owned U.S. patent application Ser. No. 09/562,815, now U.S. Pat. No. 6,387,930; and (4) related to commonly-owned, U.S. patent application Ser. No. 10/010,481, now U.S. Pat. No. 6,602,885; and (5) commonly-owned, pending U.S. patent application Ser. No. 10/061,011, filed Jan. 3, 2002.

BACKGROUND OF THE INVENTION

The present invention relates to methods of treating patients having immunodeficiency virus type-1 ("HIV-1") infections by administering a therapeutically effective amount of pegylated interferon-alfa in association with a therapeutically effective amount of a CCR5 antagonist sufficient to lower HIV-1-RNA.

The global health crisis caused by Human Immunodeficiency Virus-1 ("HIV-1"), the causative agent of Acquired Immunodeficiency Syndrome (AIDS), is unquestioned, and while recent advances in drug therapies have been successful in slowing the progression of AIDS, there is still a need to find a safer, more efficient, less expensive way to control the virus.

It has been reported that the CCR5 gene plays a role in resistance to HIV infection. HIV infection begins by attachment of the virus to a target cell membrane through interaction with the cellular receptor CD4 and a secondary chemokine co-receptor molecule, and proceeds by replication and dissemination of infected cells through the blood and other tissue. There are various chemokine receptors, but for macrophage-tropic HIV, believed to be the key pathogenic strain that replicates in vivo in the early stages of infection, the principal chemokine receptor required for the entry of HIV into the cell is CCR5. Therefore, interfering with the interaction between the viral receptor CCR5 and HIV can block HIV entry into the cell. The present invention relates to the use of small molecules which are CCR5 antagonists in assoiation with pegylated interferon-alfa to treat patients having HIV-1 infections.

A-M. Vandamme et al., *Antiviral Chemistry & Chemotherapy*, 9:187-203 (1998) disclose current clinical treatments of HIV-1 infections in man including at least triple drug combinations or so-called Highly Active Antiretroviral Therapy ("HAART"); HAART involves various combinations of nucleoside reverse transcriptase inhibitors ("NRTI"), non-nucleoside reverse transcriptase inhibitors ("NNRTI") and HIV protease inhibitors ("PI"). In compliant drug-naive patients, HAART is effective in reducing mortality and progression of HIV-1 to AIDS. However, these multidrug therapies do not eliminate HIV-1 and long-term treatment usually results in multidrug resistance. Development of new drug therapies to provide better HIV-1 treatment remains a priority.

SUMMARY OF THE INVENTION

The present invention provides a method of treating patients having HIV-1 infections which comprises administering a therapeutically effective amount of pegylated interferon-alfa in association with a therapeutically effective amount of a CCR5 antagonist sufficient to lower HIV-1-RNA plasma levels.

The present invention also provides a method of treating patients having HIV-1 infections which comprises administering a therapeutically effective amount of pegylated interferon-alfa in association with a therapeutically effective amount of a CCR5 antagonist represented by the structural formula I or II or III or IV

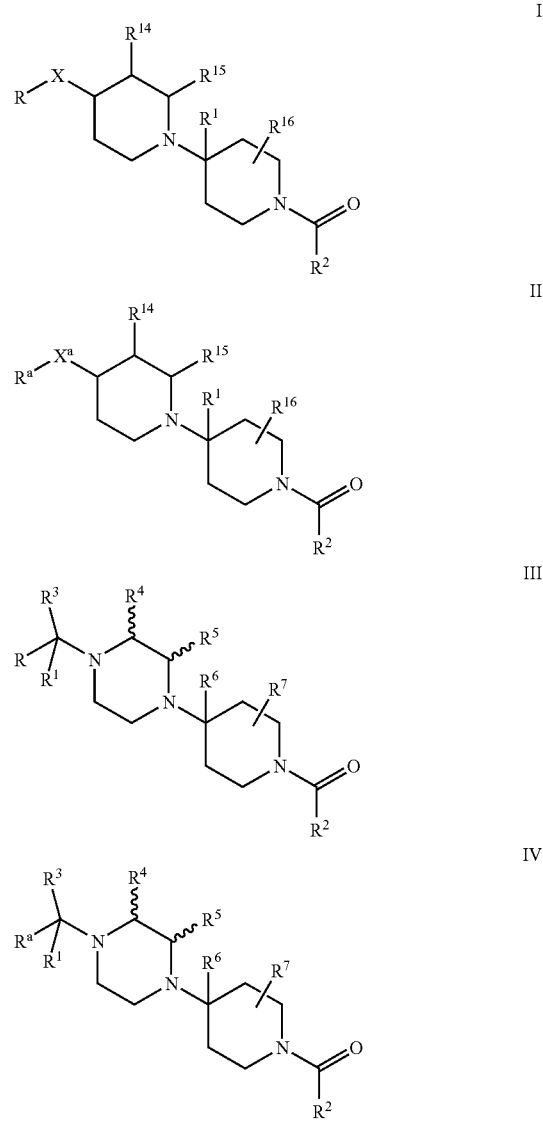

or a pharmaceutically acceptable salt of I or II or III or IV, sufficient to lower HIV-1-RNA plasma levels;

wherein in the CCR5 antagonist compounds represented by structural formula I:

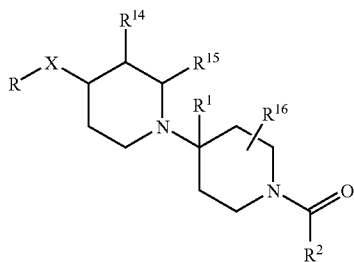

X is $-C(R^{13})_2-$, $-C(R^{13})(R^{19})-$, $-C(O)-$, $-O-$, $-NH-$, $-N((C_1-C_6)alkyl)-$,

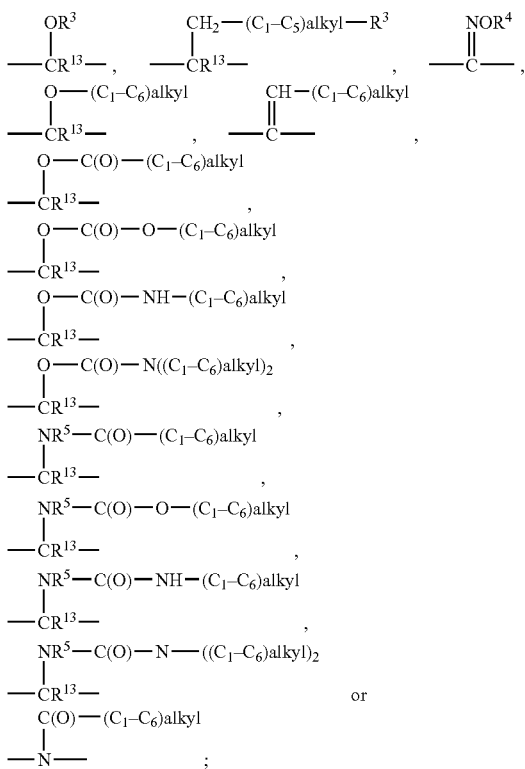

R is $R^6$-phenyl, $R^6$-pyridyl, $R^6$-thiophenyl or $R^6$-naphthyl;

$R^1$ is hydrogen, $C_1-C_6$ alkyl or $C_2-C_6$ alkenyl;

$R^2$ is $R^7$, $R^8$, $R^9$-phenyl; $R^7$, $R^8$, $R^9$-substituted 6-membered heteroaryl;

$R^7$, $R^8$, $R^9$-substituted 6-membered heteroaryl N-oxide;

$R^{10}$, $R^{11}$-substituted 5-membered heteroaryl; naphthyl; fluorenyl; diphenylmethyl

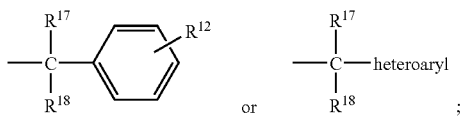

$R^3$ is $R^6$-phenyl, $R^6$-heteroaryl or $R^6$-naphthyl;

$R^4$ is hydrogen, $C_1-C_6$ alkyl, fluoro-$C_1-C_6$ alkyl, cyclopropylmethyl, $-CH_2CH_2OH$, $-CH_2CH_2-O-(C_1-C_6)alkyl$, $-CH_2C(O)-O-(C_1-C_6)alkyl$, $-CH_2C(O)NH_2$, $-CH_2C(O)-NH(C_1-C_6)alkyl$ or $-CH_2C(O)-N((C_1-C_6)alkyl)_2$;

$R^5$ and $R^{11}$ are independently selected from the group consisting of hydrogen and $(C_1-C_6)$-alkyl;

$R^6$ is 1 to 3 substituents independently selected from the group consisting of hydrogen, halogen, $C_1-C_6$ alkyl, $C_1-C_6$ alkoxy, $-CF_3$, $CF_3O-$, $CH_3C(O)-$, $-CN$, $CH_3SO_2-$, $CF_3SO_2-$, $R^{14}$-phenyl, $R^{14}$-benzyl, $CH_3C(=NOCH_3)-$, $CH_3C(=NOCH_2CH_3)-$,

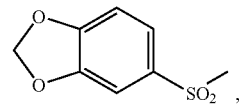

$-NH_2$, $-NHCOCF_3$, $-NHCONH(C_1-C_6$ alkyl), $-NHCO(C_1-C_6$ alkyl), $-NHSO_2(C_1-C_6$ alkyl), 5-membered heteroaryl and

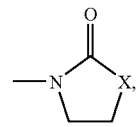

wherein X is $-O-$, $-NH-$ or $-N(CH_3)-$;

$R^7$ and $R^8$ are independently selected from the group consisting of $(C_1-C_6)$alkyl, halogen, $-NR^{20}R^{21}$, $-OH$, $-CF_3$, $-OCH_3$, $-O$-acyl, and $-OCF_3$;

$R^9$ is $R^7$, hydrogen, phenyl, $-NO_2$, $-CN$, $-CH_2F$, $-CHF_2$, $-CHO$, $-CH=NOR^{20}$, pyridyl, pyridyl N-oxide, pyrimidinyl, pyrazinyl, $-N(R^{20})CONR^{21}R^{22}$, $-NHCONH(chloro-(C_1-C_6)alkyl)$, $-NHCONH((C_3-C_{10})$-cycloalkyl$(C_1-C_6)alkyl)$, $-NHCO(C_1-C_6)alkyl$, $-NHCOCF_3$, $-NHSO_2N((C_1-C_6)alkyl)_2$, $-NHSO_2(C_1-C_6)alkyl$, $-N(SO_2CF_3)_2$, $-NHCO_2(C_1-C_6)alkyl$, $C_3-C_{10}$ cycloalkyl, $-SR^{23}$, $-SOR^{23}$, $-SO_2R^{23}$, $-SO_2NH(C_1-C_6$ alkyl), $-OSO_2(C_1-C_6)alkyl$, $-OSO_2CF_3$, hydroxy$(C_1-C_6)alkyl$, $-CON R^{20}R^{21}$, $-CON(CH_2CH_2-O-CH_3)_2$, $-OCONH(C_1-C_6)alkyl$, $-CO_2R^{20}$, $-Si(CH_3)_3$ or $-B(OC(CH_3)_2)_2$;

$R^{10}$ is $(C_1-C_6)$alkyl, $-NH_2$ or $R^{12}$-phenyl;

$R^{12}$ is 1 to 3 substituents independently selected from the group consisting of hydrogen, $(C_1-C_6)$ alkyl, $-CF_3$, $-CO_2R^{20}$, $-CN$, $(C_1-C_6)$alkoxy and halogen;

$R^{13}$, $R^{14}$, $R^{15}$ and $R^{16}$ are independently selected from the group consisting of hydrogen and $(C_1-C_6)$alkyl;

$R^{17}$ and $R^{18}$ are independently selected from the group consisting of hydrogen and $C_1-C_6$ alkyl, or $R^{17}$ and $R^{18}$ together are a $C_2-C_5$ alkylene group and with the carbon to which they are attached form a spiro ring of 3 to 6 carbon atoms;

$R^{19}$ is $R^6$-phenyl, $R^6$-heteroaryl, $R^6$-naphthyl, $C_3-C_{10}$ cycloalkyl, $(C_3-C_{10})$cycloalkyl$(C_1-C_6)$alkyl or $(C_1-C_6)$ alkoxy$(C_1-C_6)$alkyl;

$R^{20}$, $R^{21}$ and $R^{22}$ are independently selected from the group consisting of H and $C_1-C_6$ alkyl; and $R^{23}$ is $C_1-C_6$ alkyl or phenyl;

and wherein in the CCR5 antagonist compounds represented by the structural formula II:

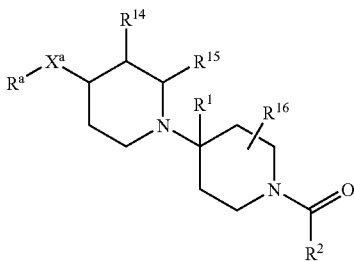

or a pharmaceutically acceptable salt thereof, wherein
(1) $X^a$ is $-C(R^{13})_2-$, $-C(R^{13})(R^{19})-$, $-C(O)-$, $-O-$, $-NH-$, $-N((C_1-C_6)alkyl)-$,

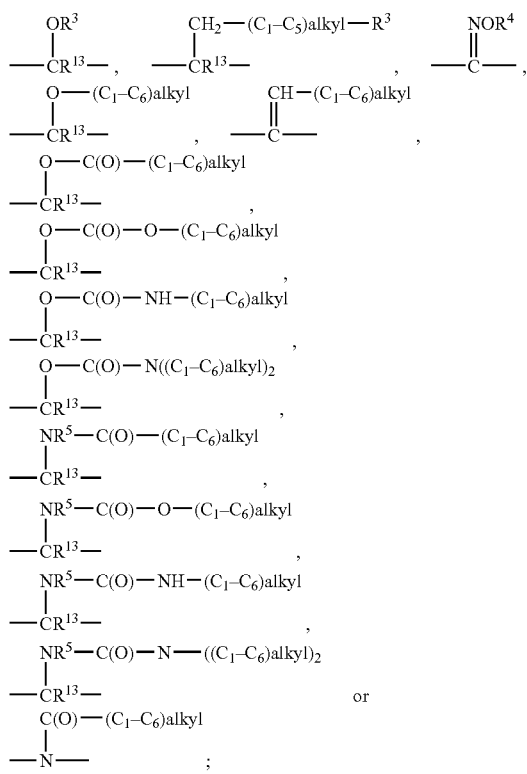

$R^a$ is $R^{6a}$-phenyl, $R^{6a}$-pyridyl, $R^{6a}$-thiophenyl or $R^6$-naphthyl;

$R^1$ is hydrogen, $C_1$-$C_6$ alkyl or $C_2$-$C_6$ alkenyl;

$R^2$ is $R^7$, $R^8$, $R^9$-phenyl; $R^7$, $R^8$, $R^9$-substituted 6-membered heteroaryl;

$R^7$, $R^8$, $R^9$-substituted 6-membered heteroaryl N-oxide;

$R^{10}$, $R^{11}$-substituted 5-membered heteroaryl; naphthyl; fluorenyl; diphenylmethyl

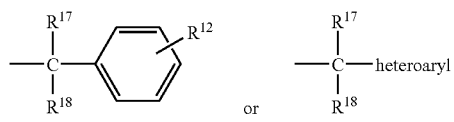

$R^3$ is $R^{10}$-phenyl, pyridyl, pyrimidyl, pyrazinyl or thiazolyl;

$R^4$ is hydrogen, $C_1$-$C_6$ alkyl, fluoro-$C_1$-$C_6$ alkyl, cyclopropylmethyl, $-CH_2CH_2OH$, $-CH_2CH_2-O-(C_1-C_6)alkyl$, $-CH_2C(O)-O-(C_1-C_6)alkyl$, $-CH_2C(O)NH_2$, $-CH_2C(O)-NH(C_1-C_6)alkyl$ or $-CH_2C(O)-N((C_1-C_6)alkyl)_2$;

$R^5$ and $R^{11}$ are independently selected from the group consisting of hydrogen and $(C_1-C_6)$-alkyl;

$R^{6a}$ is 1 to 3 substituents independently selected from the group consisting of hydrogen, halogen, $-CF_3$, $CF_3O-$, $-CN$, $-CF_3SO_2-$, $R^{12}$-phenyl, $-NHCOCF_3$, 5-membered heteroaryl and

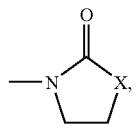

wherein X is $-O-$, $-NH-$ or $N(CH_3)-$;

$R^6$ is independently selected from the group consisting of $R^{6a}$ and $CH_3SO_2-$;

$R^7$ and $R^8$ are independently selected from the group consisting of $(C_1-C_6)alkyl$, halogen, $-NR^{20}R^{21}$, $-OH$, $-CF_3$, $-OCH_3$, $-O$-acyl, and $-OCF_3$;

$R^9$ is $R^7$, hydrogen, phenyl, $-NO_2$, $-CN$, $-CH_2F$, $-CHF_2$, $-CHO$, $-CH=NOR^{20}$, pyridyl, pyridyl N-oxide, pyrimidinyl, pyrazinyl, $-N(R^{20})CONR^{21}R^{22}$, $-NHCONH(chloro-(C_1-C_6)alkyl)$, $-NHCONH((C_3-C_{10})$-cycloalkyl$(C_1-C_6)alkyl)$, $-NHCO(C_1-C_6)alkyl$, $-NHCOCF_3$, $-NHSO_2N((C_1-C_6)alkyl)_2$, $-NHSO_2(C_1-C_6)alkyl$, $-N(SO_2CF_3)_2$, $-NHCO_2(C_1-C_6)alkyl$, $C_3$-$C_{10}$ cycloalkyl, $-SR^{23}$, $-SOR^{23}$, $-SO_2R^{23}$, $-SO_2NH(C_1-C_6$ alkyl), $-OSO_2(C_1-C_6)alkyl$, $-OSO_2CF_3$, hydroxy$(C_1-C_6)$alkyl, $-CONR^{20}R^{21}$, $-CON(CH_2CH_2-O-CH_3)_2$, $-OCONH(C_1-C_6)alkyl$, $-CO_2R^{20}$, $-Si(CH_3)_3$ or $-B(OC(CH_3)_2)_2$;

$R^{10}$ is $(C_1-C_6)alkyl$, $-NH_2$ or $R^{12}$-phenyl;

$R^{12}$ is 1 to 3 substituents independently selected from the group consisting of hydrogen, $(C_1-C_6)$ alkyl, $-CF_3$, $-CO_2R_{20}$, $-CN$, $(C_1-C_6)alkoxy$ and halogen;

$R^{13}$, $R^{14}$, $R^{15}$ and $R^{16}$ are independently selected from the group consisting of hydrogen and $(C_1-C_6)alkyl$;

$R^{17}$ and $R^{18}$ are independently selected from the group consisting of hydrogen and $C_1$-$C_6$ alkyl, or $R^{17}$ and $R^{18}$ together are a $C_2$-$C_5$ alkylene group and with the carbon to which they are attached form a spiro ring of 3 to 6 carbon atoms;

$R^{19}$ is $R^6$-phenyl, $R^6$-heteroaryl, $R^6$-naphthyl, $C_3$-$C_{10}$cycloalkyl, $(C_3-C_{10})$cycloalkyl$(C_1-C_6)$alkyl or $(C_1-C_6)$alkoxy$(C_1-C_6)$alkyl;

$R^{20}$, $R^{21}$ and $R^{22}$ are independently selected from the group consisting of H and $C_1$-$C_6$ alkyl; and $R^{23}$ is $C_1$-$C_6$ alkyl or phenyl; or (2):

$X^a$ is $-C(R^{13})(R^{19})-$, $-C(O)-$, $-O-$, $-NH-$, $-N((C_1-C_6)alkyl)-$,

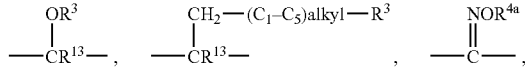

-continued

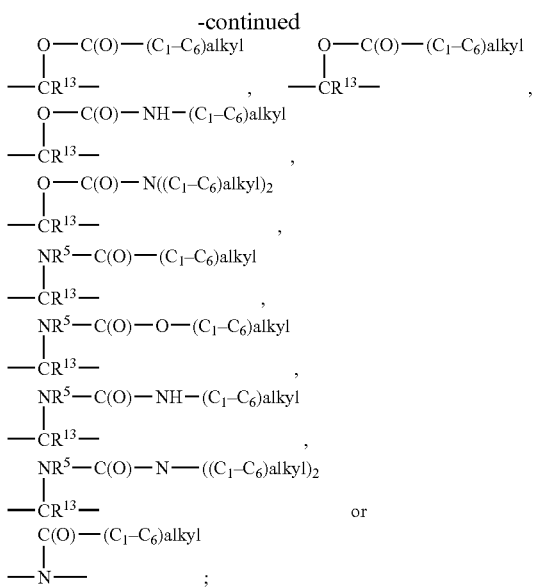

$R^a$ is $R^{6b}$-phenyl, $R^{6b}$-pyridyl or $R^{6b}$-thiophenyl;
$R^{4a}$ is fluoro-$C_1$-$C_6$ alkyl, cyclopropylmethyl, —$CH_2CH_2OH$, —$CH_2CH_2$—O—($C_1$-$C_6$)alkyl, —$CH_2C(O)$—O—($C_1$-$C_6$)alkyl, —$CH_2C(O)NH_2$, —$CH_2C(O)$—NH—($C_1$-$C_6$)alkyl or —$CH_2C(O)$—N(($C_1$-$C_6$)alkyl)$_2$;
$R^{6b}$ is $CH_3SO_2$—; and
$R^1$, $R^2$, $R^3$, $R^5$, $R^{14}$, $R^{15}$, $R^{16}$ and $R^{19}$ are as defined in II(1);
and wherein in the CCR5 antagonist compounds represented by the structural formula III:

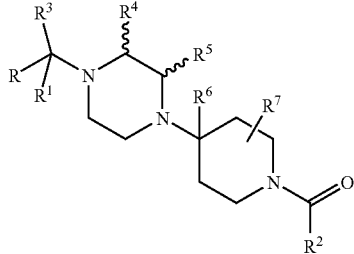

R is $R^8$-phenyl, $R^8$-pyridyl, $R^8$-thiophenyl or $R^8$-naphthyl;
$R^1$ is hydrogen or $C_1$-$C_6$ alkyl;
$R^2$ is $R^9$, $R^{10}$, $R^{11}$-phenyl; $R^9$, $R^{10}$, $R^{11}$-substituted 6-membered heteroaryl; $R^9$, $R^{10}$, $R^{11}$-substituted 6-membered heteroaryl N-oxide;
$R^{12}$, $R^{13}$-substituted 5-membered heteroaryl; naphthyl; fluorenyl; diphenylmethyl

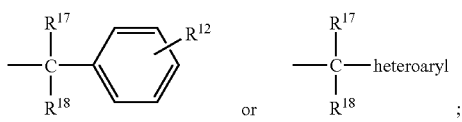

$R^3$ is hydrogen, $C_1$-$C_6$ alkyl, ($C_1$-$C_6$)alkoxy($C_1$-$C_6$)alkyl, $C_3$-$C_{10}$ cycloalkyl, $C_3$-$C_{10}$ cycloalkyl($C_1$-$C_6$)alkyl, $R^8$-phenyl, $R^8$-phenyl($C_1$-$C_6$)alkyl, $R^8$-naphthyl, $R^8$-naphthyl($C_1$-$C_6$)alkyl, $R^8$-heteroaryl or $R^8$-heteroaryl($C_1$-$C_6$)alkyl;
$R^4$, $R^5$, $R^7$ and $R^{13}$ are independently selected from the group consisting of hydrogen and ($C_1$-$C_6$)-alkyl;
$R^6$ is hydrogen, $C_1$-$C_6$ alkyl or $C_2$-$C_6$ alkenyl;
$R^8$ is 1 to 3 substituents independently selected from the group consisting of hydrogen, halogen, $C_1$-$C_6$ alkyl, $C_1$-$C_6$ alkoxy, —$CF_3$, $CF_3O$—, $CH_3C(O)$—, —CN, $CH_3SO_2$—, $CF_3SO_2$—, $R^{14}$-phenyl, $R^{14}$-benzyl, $CH_3C(=NOCH_3)$, $CH_3C(=NOCH_2CH_3)$,

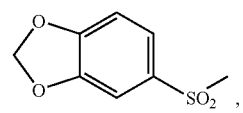

—$NH_2$, —$NHCOCF_3$, —$NHCONH(C_1$-$C_6$ alkyl), —NHCO($C_1$-$C_6$ alkyl), —$NHSO_2(C_1$-$C_6$ alkyl), 5-membered heteroaryl and

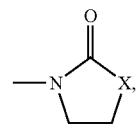

wherein X is —O—, —NH— or —N($CH_3$)—;
$R^9$ and $R^{10}$ are independently selected from the group consisting of ($C_1$-$C_6$)alkyl, halogen, —$NR^{17}R^{18}$, —OH, —$CF_3$, —$OCH_3$, —O-acyl, —$OCF_3$ and —Si($CH_3$)$_3$;
$R^{11}$ is $R^9$, hydrogen, phenyl, —$NO_2$, —CN, —$CH_2F$, —$CHF_2$, —CHO, —CH=$NOR^{17}$, pyridyl, pyridyl N-oxide, pyrimidinyl, pyrazinyl, —$N(R^{17})CONR^{18}R^{19}$, —NHCONH(chloro-($C_1$-$C_6$)alkyl), —NHCONH(($C_3$-$C_1$)cycloalkyl($C_1$-$C_6$)alkyl), —NHCO($C_1$-$C_6$)alkyl, —$NHCOCF_3$, —$NHSO_2N(($C_1$-$C_6$)alkyl)$_2$, —$NHSO_2(C_1$-$C_6$)alkyl, —N($SO_2CF_3$)$_2$, —$NHCO_2(C_1$-$C_6$)alkyl, $C_3$-$C_{10}$ cycloalkyl, —$SR^{20}$, —$SOR^{20}$, —$SO_2R^{20}$, —$SO_2NH(C_1$-$C_6$ alkyl), —$OSO_2(C_1$-$C_6$)alkyl, —$OSO_2CF_3$, hydroxy($C_1$-$C_6$) alkyl, —$CON R^{17}R^{18}$, —$CON(CH_2CH_2$—O—$CH_3$)$_2$, —$OCONH(C_1$-$C_6$)alkyl, —$CO_2R$ , —$Si(CH_3)_3$ or —$B(OC(CH_3)_2)_2$;
$R^{12}$ is ($C_1$-$C_6$)alkyl, —$NH_2$ or $R^{14}$-phenyl;
$R^{14}$ is 1 to 3 substituents independently selected from the group consisting of hydrogen, ($C_1$-$C_6$) alkyl, —$CF_3$, —$CO_2R^{17}$, —CN, ($C_1$-$C_6$)alkoxy and halogen;
$R^{15}$ and $R^{16}$ are independently selected from the group consisting of hydrogen and $C_1$-$C_6$ alkyl, or $R^{15}$ and $R^{16}$ together are a $C_2$-$C_5$ alkylene group and with the carbon to which they are attached form a spiro ring of 3 to 6 carbon atoms;
$R^{17}$, $R^{18}$ and $R^{19}$ are independently selected from the group consisting of H and $C_1$-$C_6$ alkyl; and
$R^{20}$ is $C_1$-$C_6$ alkyl or phenyl;
and wherein in the CCR5 antagonist compounds represented by the structural formula IV:

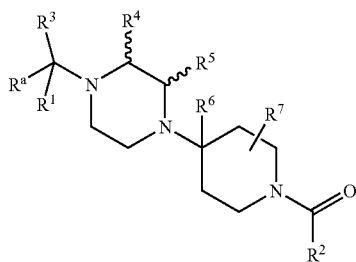

IV or a pharmaceutically acceptable salt thereof, wherein
(1) $R^a$ is $R^{8a}$-phenyl, $R^{8b}$-pyridyl, $R^{8b}$-thiophenyl or $R^8$-naphthyl;

$R^1$ is hydrogen or $C_1$-$C_6$ alkyl;

$R^2$ is $R^9$, $R^{10}$, $R^{11}$-phenyl; $R^9$, $R^{10}$, $R^{11}$-substituted 6-membered heteroaryl; $R^9$, $R^{10}$, $R^{11}$-substituted 6-membered heteroaryl N-oxide;

$R^{12}$, $R^{13}$-substituted 5-membered heteroaryl; naphthyl; fluorenyl;

diphenylmethyl

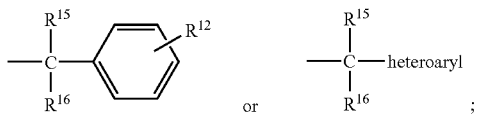

$R^3$ is hydrogen, $C_1$-$C_6$ alkyl, $(C_1$-$C_6)$alkoxy$(C_1$-$C_6)$alkyl, $C_3$-$C_{10}$ cycloalkyl, $C_3$-$C_{10}$ cycloalkyl$(C_1$-$C_6)$alkyl, $R^8$-phenyl, $R^8$-phenyl$(C_1$-$C_6)$alkyl, $R^8$-naphthyl, $R^8$-naphthyl$(C_1$-$C_6)$alkyl, $R^8$-heteroaryl or $R^8$-heteroaryl$(C_1$-$C_6)$alkyl;

$R^4$, $R^5$, $R^7$ and $R^{13}$ are independently selected from the group consisting of hydrogen and $(C_1$-$C_6)$-alkyl;

$R^6$ is hydrogen, $C_1$-$C_6$ alkyl or $C_2$-$C_6$ alkenyl;

$R^8$ is 1 to 3 substituents independently selected from the group consisting of hydrogen, halogen, $C_1$-$C_6$ alkyl, $C_1$-$C_6$ alkoxy, —$CF_3$, $CF_3O$—, $CH_3C(O)$—, —CN, $CH_3SO_2$—, $CF_3SO_2$—, $R^{14}$-phenyl, $R^{14}$-benzyl, $CH_3C(=NOCH_3)$, $CH_3C(=NOCH_2CH_3)$,

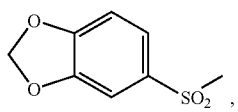

—$NH_2$, —$NHCOCF_3$, —$NHCONH(C_1$-$C_6$ alkyl), —NHCO$(C_1$-$C_6$ alkyl), —$NHSO_2(C_1$-$C_6$ alkyl), 5-membered heteroaryl and

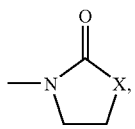

wherein X is —O—, —NH— or —$N(CH_3)$—;

$R^{8a}$ is 1 to 3 substituents independently selected from the group consisting of hydrogen, halogen, —$CF_3$, $CF_3O$—, —CN, $CF_3SO_2$—, $R^{14}$-phenyl, —$NHCOCF_3$, 5-membered heteroaryl and

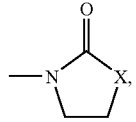

wherein X is as defined above;

$R^{8b}$ is 1 to 3 substituents independently selected from the group consisting of hydrogen, halogen, —$CF_3$, $CF_3O$—, $CH_3C(O)$—, —CN, $CF_3SO_2$—, $R^{14}$-benzyl, $CH_3C(=NOCH_3)$, $CH_3C(=NOCH_2CH_3)$,

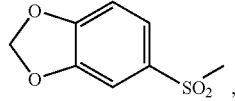

—$NHCOCF_3$, 5-membered heteroaryl and

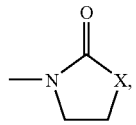

wherein X is as defined above;

$R^9$ and $R^{10}$ are independently selected from the group consisting of $(C_1$-$C_6)$alkyl, halogen, —$NR^{17}R^{18}$, —OH, —$CF_3$, —$OCH_3$, —O-acyl, —$OCF_3$ and —Si$(CH_3)_3$;

$R^{11}$ is $R^9$, hydrogen, phenyl, —$NO_2$, —CN, —$CH_2F$, —$CHF_2$, —CHO, —CH=$NOR^{17}$, pyridyl, pyridyl N-oxide, pyrimidinyl, pyrazinyl, —$N(R^{17})$CONR$^{18}$R$^{19}$, —NHCONH(chloro-$(C_1$-$C_6)$alkyl), —NHCONH(($C_3$-$C_1$)cycloalkyl$(C_1$-$C_6)$alkyl), —NHCO$(C_1$-$C_6)$alkyl, —$NHCOCF_3$, —$NHSO_2$N(($C_1$-$C_6)$alkyl)$_2$, —$NHSO_2(C_1$-$C_6)$alkyl, —N(SO$_2$CF$_3$)$_2$, —$NHCO_2(C_1$-$C_6)$alkyl, $C_3$-$C_{10}$ cycloalkyl, SR$^{20}$, —SOR$^{20}$, —SO$_2$R$^{20}$, —SO$_2$NH$(C_1$-$C_6$ alkyl), —OSO$_2(C_1$-$C_6)$alkyl, —$OSO_2CF_3$, hydroxy$(C_1$-$C_6)$ alkyl, —CON R$^{17}$R$^{18}$, —CON(CH$_2$CH$_2$—O—CH$_3$)$_2$, —OCONH$(C_1$-$C_6)$alkyl, —$CO_2R^{17}$, —Si(CH$_3$)$_3$ or —B(OC(CH$_3$)$_2$)$_2$;

$R^{12}$ is $(C_1$-$C_6)$alkyl, —$NH_2$ or $R^{14}$-phenyl;

$R^{14}$ is 1 to 3 substituents independently selected from the group consisting of hydrogen, $(C_1$-$C_6)$ alkyl, —$CF_3$, —$CO_2R_{17}$, —CN, $(C_1$-$C_6)$alkoxy and halogen;

$R^{15}$ and $R^{16}$ are independently selected from the group consisting of hydrogen and $C_1$-$C_6$ alkyl, or $R^{15}$ and $R^{16}$ together are a $C_2$-$C_5$ alkylene group and with the carbon to which they are attached form a spiro ring of 3 to 6 carbon atoms;

$R^{17}$, $R^{18}$ and $R^{19}$ are independently selected from the group consisting of H and $C_1$-$C_6$ alkyl; and $R^{20}$ is $C_1$-$C_6$ alkyl or phenyl; or (2) $R^a$ is $R^8$-phenyl, $R^8$-pyridyl or $R^8$-thiophenyl;

$R^2$ is fluorenyl,

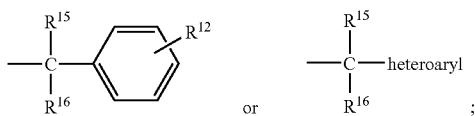

and $R^1$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$ and $R^{20}$ are as defined in IV(1).

Preferred are compounds of formula I wherein R is $R^6$-phenyl, especially wherein $R^6$ is a single substituent, and especially wherein the $R^6$ substituent is in the 4-position. Also preferred are compounds of formula I wherein $R^{13}$, $R^{14}$, $R^{15}$ and $R^{16}$ are each hydrogen or methyl, especially hydrogen. Also preferred are compounds of formula I wherein X is —CHOR³—, —C(R¹³)(R¹⁹)— or —C(=NOR⁴)—; a preferred definition for $R^3$ is pyridyl, especially 2-pyridyl, a preferred definition for $R^4$ is $(C_1-C_6)$ alkyl, especially methyl, ethyl or isopropyl, a preferred definition for $R^{13}$ is hydrogen, and a preferred definition for $R^{19}$ is $R^6$-phenyl. For compounds of formula I, $R^1$ is preferably $(C_1-C_6)$alkyl, especially methyl.

In compounds of formula I, $R^2$ is preferably $R^7$, $R^8$, $R^9$-phenyl, $R^7$, $R^8$, $R^9$-pyridyl or an N-oxide thereof, or $R^7$, $R^8$, $R^9$-pyrimidyl. When $R^2$ is pyridyl, it is preferably 3- or 4-pyridyl, and when pyrimidyl, it is preferably 5-pyrimidyl. The $R^7$ and $R^8$ substituents are preferably attached to carbon ring members adjacent to the carbon joining the ring to the rest of the molecule and the $R^9$ substituent can be attached to any of the remaining unsubstituted carbon ring members, for example as shown in the following structures:

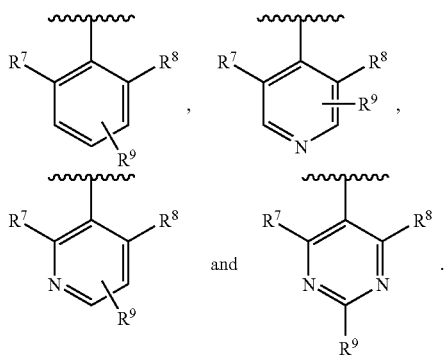

Preferred $R^7$ and $R^8$ substituents are: $(C_1-C_6)$alkyl, especially methyl; halogen, especially chloro; and —NH₂. A preferred $R^9$ substituent is hydrogen.

Preferred are compounds of formula II(1) wherein $R^a$ is $R^{6a}$-phenyl, especially wherein $R^{6a}$ is a single substituent, and especially wherein the $R^{6a}$ substituent is in the 4-position. Also preferred are compounds of formula II(1) wherein $X^a$ is —CHOR³—, —C(R¹³)(R¹⁹)— or —C(=NOR⁴)—; a preferred definition for $R^3$ is pyridyl, especially 2-pyridyl, a preferred definition for $R^4$ is $(C_1-C_6)$alkyl, especially methyl, ethyl or isopropyl, a preferred definition for $R^{13}$ is hydrogen, and a preferred definition for $R^{19}$ is $R^6$-phenyl. For compounds of formula II(1), $R^1$ is preferably $(C_1-C_6)$ alkyl, especially methyl. Also for compounds of formula II(1), $R^{14}$, $R^{15}$ and $R^{16}$ are preferably hydrogen.

Preferred are compounds of formula II(2) wherein $R^a$ is $R^{6b}$-phenyl, especially wherein $R^{6b}$ is a single substituent, and especially wherein the $R^{6b}$ substituent is in the 4-position. Also preferred are compounds of formula II(2) wherein $X^a$ is —CHOR³—, —C(R¹³)(R¹⁹)— or —C(=NOR⁴ᵃ)—; a preferred definition for $R^3$ is pyridyl, especially 2-pyridyl, preferred definitions for $R^{4a}$ are cyclopropylmethyl and trifluoroethyl, a preferred definition for $R^{13}$ is hydrogen, and a preferred definition for $R^{19}$ is $R^6$-phenyl. For compounds of formula II(2), $R^1$ is preferably $(C_1-C_6)$alkyl, especially methyl. Also for compounds of formula II(2), $R^{14}$, $R^{15}$ and $R^{16}$ are preferably hydrogen.

In compounds of formula II(1) and (2), $R^2$ is preferably $R^7$, $R^8$, $R^9$-phenyl; $R^7$, $R^8$, $R^9$-pyridyl or an N-oxide thereof; or $R^7$, $R^8$, $R^9$-pyrimidyl. When $R^2$ is pyridyl, it is preferably 3- or 4-pyridyl, and when pyrimidyl, it is preferably 5-pyrimidyl. The $R^7$ and $R^8$ substituents are preferably attached to carbon ring members adjacent to the carbon joining the ring to the rest of the molecule and the $R^9$ substituent can be attached to any of the remaining unsubstituted carbon ring members as shown above for compounds of formula I. Preferred $R^7$ and $R^8$ substituents for compounds of formula II are: $(C_1-C_6)$alkyl, especially methyl; halogen, especially chloro; and —NH₂; a preferred $R^9$ substituent is hydrogen.

Preferred are compounds of formula III wherein R is $R^8$-phenyl or $R^8$-naphthyl, especially wherein $R^8$ is a single substituent, and especially wherein the $R^8$ substituent is in the 4-position. For $R^8$-phenyl, preferred $R^8$ substituents are —CF₃, —OCF₃, CH₃SO₂—, CH₃CO—, CH₃C(=NOCH₃)—, Br and I. For $R^8$-naphthyl, $R^8$ is preferably $C_1-C_6$ alkoxy. Also preferred are compounds of formula III wherein $R^3$ is hydrogen, $(C_1-C_6)$ alkyl, $R^8$-phenyl. $R^8$-benzyl or $R^8$-pyridyl; more preferred definitions for $R^3$ are methyl, ethyl, phenyl, benzyl and pyridyl. $R^1$ is preferably hydrogen. For compounds of formula III, $R^6$ is preferably hydrogen or methyl, especially methyl. $R^4$ is preferably methyl; $R^5$ and $R^7$ are each preferably hydrogen.

In compounds of formula III, $R^2$ is preferably $R^9$, $R^{10}$, $R^{11}$-phenyl, $R^9$, $R^{10}$, $R^{11}$-pyridyl or an N-oxide thereof, or $R^9$, $R^{10}$, $R^{11}$-pyrimidyl. When $R^2$ is pyridyl, it is preferably 3- or 4-pyridyl, and when pyrimidyl, it is preferably 5-pyrimidyl. The $R^9$ and $R^{10}$ substituents are preferably attached to carbon ring members adjacent to the carbon joining the ring to the rest of the molecule and the $R^{11}$ substituent can be attached to any of the remaining unsubstituted carbon ring members, for example as shown in the following structures:

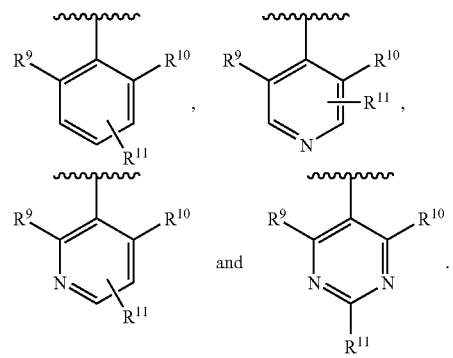

Preferred $R^9$ and $R^{10}$ substituents are: $(C_1-C_6)$alkyl, especially methyl; halogen, especially chloro or bromo, —OH and —NH₂. When $R^2$ is phenyl, $R^{11}$ is preferably hydrogen or —OH; when $R^2$ is pyridyl, $R^{11}$ is preferably hydrogen;

and when $R^2$ is pyrimidyl, $R^{11}$ is preferably hydrogen, methyl or phenyl. Examples of particularly preferred $R^2$ groups are as follows:

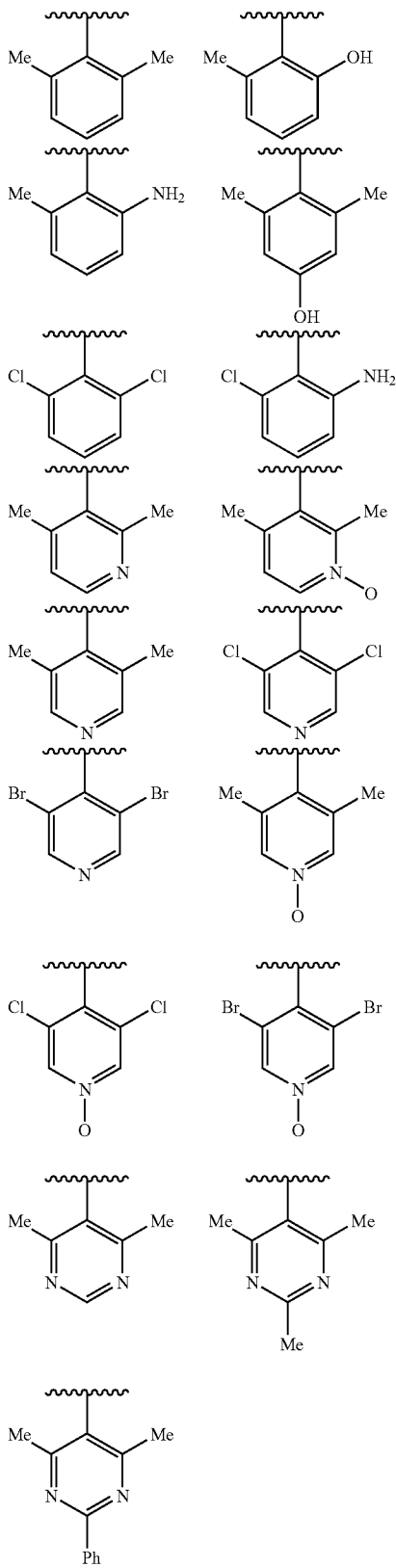

Preferred compounds of formula IV are those defined in (1).

More preferred are those of formula IV(1) wherein $R^a$ is $R^{8a}$-phenyl or $R^8$-naphthyl, wherein $R^{8a}$ is —$CF_3$, $CF_3O$— or halogen and $R^8$ is $C_1$-$C_6$ alkoxy. The $R^{8a}$ or $R^8$ substituent is preferably a single substituent; it is especially preferred that the $R^{8a}$ or $R^8$ substituent is in the 4-position. Also preferred are compounds of formula IV(1) wherein $R^3$ is hydrogen, ($C_1$-$C_6$) alkyl, $R^8$-phenyl. $R^8$-benzyl or $R^8$-pyridyl; more preferred definitions for $R^3$ are methyl, ethyl, phenyl, benzyl and pyridyl. $R^1$ is preferably hydrogen. For compounds of formula IV(1), $R^6$ is preferably hydrogen or methyl, especially methyl. $R^4$ is preferably methyl; $R^5$ and $R^7$ are each preferably hydrogen.

$R^2$ in formula IV(1) is preferably as defined for formula III, i.e., $R^9$, $R^{10}$, $R^{11}$-phenyl, $R^9$, $R^{10}$, $R^{11}$-pyridyl or an N-oxide thereof, or $R^9$, $R^{10}$, $R^{11}$-pyrimidyl, wherein the $R^9$, $R^{10}$, $R^{11}$-substitution is as defined above for preferred compounds of formula III.

The present invention also provides a method of treating patients co-infected with HIV-1 and HCV which comprises administering a therapeutically effective amount of pegylated interferon-alfa in association with a therapeutically effective amount of ribavirin and a therapeutically effective amount of HAART and a therapeutically effective amount of a CCR5 antagonist represented by the structural formula I or II or III or IV:

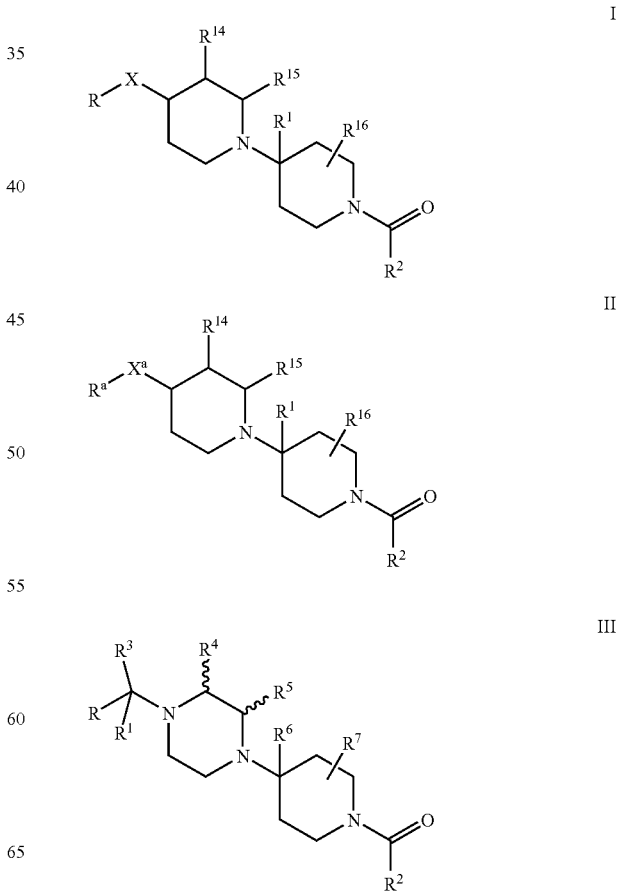

-continued

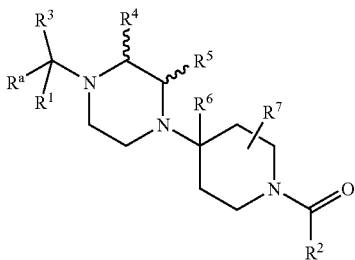

IV or a pharmaceutical salt of a compound of the formula I or II or III or IV;

sufficient to lower HIV-1-RNA and HCV-RNA plasma levels.

wherein X, R, and $R^1$ to $R^{16}$ are as defined in formula I; and wherein X, $R^a$, and $R^1$ to $R^{16}$ are as defined in formula II(1) and II(2) and wherein R, and $R^1$ to $R^{17}$ are as defined in formula III; and wherein $R^a$, and $R^1$ to $R^{17}$ are as defined in formula IV.

The present invention also provides a method of treating pediatric patients having HIV-1 infections which comprises administering a therapeutically effective amount of pegylated interferon-alfa in association with a therapeutically effective amount of HAART and a therapeutically effective amount of a CCR5 antagonist represented by the structural formula I or II or III or IV:

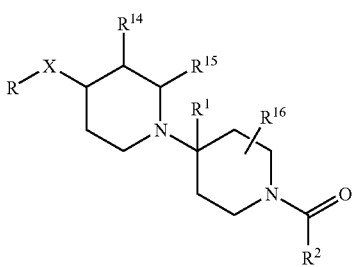

I

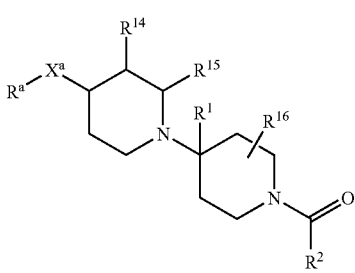

II

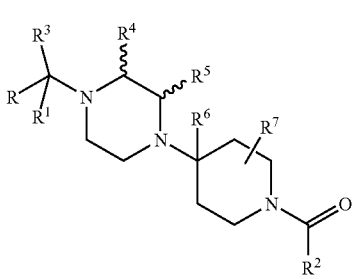

III

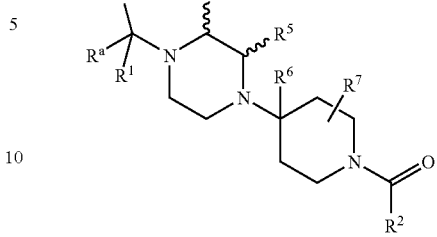

IV or a pharmaceutical salt of compounds I or II;

sufficient to lower HIV-1-RNA plasma levels.

wherein X, R, and $R^1$ to $R^{16}$ are as defined in I; and wherein $X^a$, $R^a$, and $R^1$ to $R^{16}$ are as defined in II(1) and II(2);

wherein R, and $R^1$ to $R^{17}$ are as defined in formula III; and wherein $R^a$, and $R^1$ to $R^{17}$ are as defined in formula IV.

DETAILED DESCRIPTION

As used herein, the following terms are used as defined below unless otherwise indicated.

Alkyl (including the alkyl portions of alkoxy, alkylamino and dialkylamino) represents straight and branched carbon chains and contains from one to six carbon atoms.

Alkenyl represents $C_2$-$C_6$ carbon chains having one or two unsaturated bonds, provided that two Unsaturated bonds are not adjacent to each other.

Substituted phenyl means that the phenyl group can be substituted at any available position on the phenyl ring.

Acyl means a radical of a carboxylic acid having the formula alkyl-C(O)—, aryl-C(O)—, aralkyl-C(O)—, ($C_3$-$C_7$)cycloalkyl-C(O)—, ($C_3$-$C_7$)cycloalkyl($C_1$-$C_6$)alkyl-C(O)—, and heteroaryl-C(O)—, wherein alkyl and heteroaryl are as defined herein; aryl is $R^{12}$-phenyl or $R^{12}$-naphthyl; and aralkyl is aryl-($C_1$-$C_6$)alkyl, wherein aryl is as defined above.

Heteroaryl represents cyclic aromatic groups of 5 or 6 atoms or bicyclic groups of 11 to 12 atoms having one or two heteroatoms independently selected from O, S or N, said heteroatom(s) interrupting a carbocyclic ring structure and having a sufficient number of delocalized pi electrons to provide aromatic character. For 6-membered heteroaryl rings, carbon atoms can be substituted by $R^7$, $R^8$ or $R^9$ groups. Nitrogen atoms can form an N-oxide. All regioisomers are contemplated, e.g., 2-pyridyl, 3-pyridyl and 4-pyridyl. Typical 6-membered heteroaryl groups are pyridyl, pyrimidinyl, pyrazinyl, pyridazinyl and the N-oxides thereof. For 5-membered heteroaryl rings, carbon atoms can be substituted by $R^{10}$ or $R^{11}$ groups. Typical 5-membered heteroaryl rings are furyl, thienyl, pyrrolyl, thiazolyl, isothiazolyl, imidazolyl, pyrazolyl and isoxazolyl. 5-Membered rings having one heteroatom can be joined through the 2- or 3-position; 5-membered rings having two heteroatoms are preferably joined through the 4-position. Bicyclic groups typically are benzo-fused ring systems derived from the heteroaryl groups named above, e.g. quinolyl, phthalazinyl, quinazolinyl, benzofuranyl, benzothienyl and indolyl.

Preferred points of substitution for 6-membered heteroaryl rings at $R^2$ are described above. When $R^2$ is a 5-membered heteroaryl group, the $R^{10}$ and $R^{11}$ substituents are preferably attached to carbon ring members adjacent to the carbon joining the ring to the rest of the molecule, and $R^{11}$ is preferably alkyl; however, if a heteroatom is adjacent to the carbon joining the ring to the rest of the molecule (i.e., as in 2-pyrrolyl), $R^{10}$ is preferably attached to a carbon ring member adjacent to the carbon joining the ring to the rest of the molecule.

Halogen represents fluoro, chloro, bromo and iodo.

Fluoro($C_1$-$C_6$)alkyl represents a straight or branched alkyl chain substituted by 1 to 5 fluoro atoms, which can be attached to the same or different carbon atoms, e.g., —$CH_2F$, —$CHF_2$, —$CF_3$, $F_3CCH_2$— and —$CF_2CF_3$.

The present method of treating patients having HIV-1 infections comprises administrating a therapeutically effective amount of pegylated interferon-alfa and a pegylated interferon alpha and a CCR5 antagonist of formulas I to IV is administered to a patient infected with HIV-1, or co-infected with HIV-1 and HCV, in association with ribavirin and HAART. It is a special feature of the present invention that each of pegylated interferon alpha, the CCR5 antagonists of formulas I to IV and the components of HAART has a different mechanism of action in treating HIV-1. It is another special feature of the present invention that the pegylated interferon alpha and the CCR5 antagonists of formulas I to IV do not cause cross-resistance with each other or with the components of HAART. The initiation of the administration of a therapeutically effective amount of the combination of a pegylated interferon alpha, ribavirin and a CCR5 antagonist compound represented by structural formula I or II or III or IV and HAART may occur before, after or concurrently with administering a therapeutically effective amount of combination of a pegylated interferon-alfa and a CCR5 antagonist compound represented by structural formula I or II or III or IV in accordance with the present invention. In an embodiment of the present invention, the method of treating patients having HIV-1 infections comprises two treatment time periods. In the first treatment time period, a combination of a therapeutically effective amount of pegylated interferon-alfa and a CCR5 antagonist compound represented by structural formula I or II or III or IV is administered for a first treatment time period sufficient to lower HIV-1-RNA plasma levels, preferably by a power of 10, more preferably by at least two powers of ten, i.e., at least $10^2$, lower than the initial HIV-1-RNA plasma level. In the second treatment time period, the method entails continuing the administration of a therapeutically effective amount of a combination of pegylated interferon-alfa in association a CCR5 antagonist compound represented by structural formula I or II or III or IV and a therapeutically effective amount of HAART in accordance with good clinical practice to minimize HIV-1-RNA plasma levels. A.-M. Vandamme et al., *Antiviral Chemistry & Chemotherapy*, 9:187-203 (1998) disclose current clinical treatments of HIV-1 infections, including when to start multidrug therapy and which drugs to combine. The triple drug therapy may include two NRTIs and one PI, but there are many issues to be considered in the choice of the precise HAART for any HIV-1-RNA plasma level. In the second treatment time period, the method entails continuing the administration of a therapeutically effective amount of a combination of pegylated interferon-alfa in association a CCR5 antagonist compound represented by structural formula I or II or III or IV and a therapeutically effective amount of HAART in accordance with good clinical practice to minimize HIV-1-RNA plasma levels. A.-M. Vandamme et al., *Antiviral Chemistry & Chemotherapy*, 9:187-203 (1998) disclose current clinical treatments of HIV-1 infections, including when to start multidrug therapy and which drugs to combine. The triple drug therapy may include two NRTIs and one PI, but there are many issues to be considered in the choice of the precise HAART for any patient. See for example, Tables 1 & 2 and FIG. 2 in A-M. Vandamme et al., listed hereinabove.

The terms "CCR5 antagonist compound" and "CCR5 antagonists" as used herein mean any compound that interfers with the interaction between the viral receptor CCR5 and HIV-1 to block entry of HIV-1 into the cell. Assays, e.g., the CCR5 Membrane Binding Assay, the HIV-1 Entry and the HIV-1 Entry Replication Assays, inter alia, are presented herein after to identify a compound as a CCR5 antagonist and to determine its CCR5 antagonist activity.

The term "patients having HIV-1 infections" as used herein means any patient-including a pediatric patient-having HIV-1 infection and includes treatment-naive patients and treatment-experienced patients having the HIV-1 infection as well as treatment-naive patients and treatment-experienced patients co-infected with the HIV-1 and hepatitis C virus ("HCV").

The term "pediatric patient" as used herein means a patient below the age of 17, and normally includes those from birth to 16 years of age.

The term "treatment-naive patients" as used herein means patients having HIV-1 or co-infected with the HIV-1 and HCV who have never been treated with any anti-retroviral drugs, e.g., NRTI, NNRTI, PI or any interferon, including but not limited to interferon-alfa, or pegylated interferon alfa.

The term "treatment-experienced" patients as used herein means those patients having HIV-1 or co-infected with the HIV-1 and HCV who have initiated some form of anti HIV therapy including, but not limited to HAART or some form of anti-HCV therapy, including but not limited to interferon-alfa, pegylated interferon alfa or ribavirin.

The term "patients having hepatitis C infections" as used herein means any patient-including a pediatric patient-having hepatitis C and includes treatment-naive patients having hepatitis C infections and treatment-experienced patients having hepatitis C infections as well as those pediatric, treatment-naive and treatment-experienced patients having chronic hepatitis C infections.

These patients having hepatitis C include those who are infected with multiple HCV genotypes including type 1 as well as those infected with, e.g., HCV genotypes 2, 3, 4, 5 and/or 6 and other possible HCV genotypes.

The term "treatment-naive patients having hepatitis C infections" as used herein means patients with hepatitis C who have never been treated with ribavirin or any interferon, including but not limited to interferon-alfa, or pegylated interferon alfa.

The term "treatment-experienced patients having hepatitis C infections" as used herein means patients with hepatitis C who have been treated with ribavirin or any interferon, including but not limited to interferon-alfa, or pegylated interferon alfa, including relapsers and non-responder.

The term "relapsers" as used herein means treatment-experienced patients with hepatitis C who have relapsed after initial response to previous treatment with interferon alone, or in combination with ribavirin.

The term "non-responders" as used herein means treatment-experienced patients with hepatitis C who have not responded to prior treatment with any interferon alone, or in combination with ribavirin.

When the pegylated interferon-alfa administered is a pegylated interferon alfa-2b, the therapeutically effective amount of pegylated interferon alfa-2b administered during the treatment in accordance with the present invention, including in first and second treatment time periods, is in the range of about 0.1 to 9.0 micrograms per kilogram of pegylated interferon alfa-2b administered per week, in single or divided doses, preferably once a week (QW) or twice a week(BIW), preferably in the range of about 0.1 to about 9.0 micrograms per kilogram of pegylated interferon alfa-2b administered once a week (QW) or in the range of about 0.05 to about 4.5 micrograms per kilogram of pegylated interferon alfa-2b administered twice a week(BIW), or is in the range of about 0.5 to about 3.0 micrograms per kilogram of pegylated interferon alfa-2b administered per week, preferably in the range of about 0.5 to about 3.0 micrograms per kilogram of pegylated interferon alfa-2b administered once a week (QW) or in the range of about 0.25 to about 1.5 micrograms per kilogram of pegylated interferon alfa-2b administered twice a week, or is in the range of about 0.75 to about 1.5 micrograms per kilogram of pegylated interferon alfa-2b administered per week, most preferably is in the range of about 0.75 to about 1.5 micrograms per kilogram of pegylated interferon alfa-2b administered once a week or about 0.375 to about 0.75 micrograms per kilogram of pegylated interferon alfa-2b administered twice a week.

When the pegylated interferon-alfa administered to pediatric patients is a pegylated interferon alfa-2b, the therapeutically effective amount of pegylated interferon alfa-2b administered during the treatment in accordance with the present invention, including in first and second treatment time periods is in the range of about 0.1 to 9.0 micrograms per kilogram of pegylated interferon alfa-2b administered per week, in single or divided doses, preferably once a week (QW) or twice a week(BIW), more preferably about 0.1 to about 9.0 micrograms per kilogram of pegylated interferon alfa-2b administered once a week (QW), or about 0.05 to about 4.5 micrograms per kilogram of pegylated interferon alfa-2b administered per week, in single or divided doses, preferably once a week (QW) or twice a week(BIW), more preferably about 0.05 to about 4.5 micrograms per kilogram of pegylated interferon alfa-2b administered once a week, or preferably about 0.75 to about 3.0 micrograms per kilogram of pegylated interferon alfa-2b administered in single or divided doses, preferably once a week (QW) or twice a week(BIW), more preferably about 0.75 to about 3.0 micrograms per kilogram of pegylated interferon alfa-2b administered once a week or about 0.375 to about 1.5 micrograms per kilogram of pegylated interferon alfa-2b administered twice a week, and most preferably about 2.25 to about 2.6 micrograms per kilogram of pegylated interferon alfa-2b administered once a week or about 1.1 to about 1.3 micrograms per kilogram of pegylated interferon alfa-2b administered twice a week(BIW).

When the pegylated interferon-alfa administered is a pegylated interferon alfa-2a, the therapeutically effective amount of pegylated interferon alfa-2a administered during the treatment in accordance with the present invention, including in first and second treatment time periods, is in the range of about 50 micrograms to about 500 micrograms per week, preferably about 150 micrograms to about 250 micrograms per week, or preferably about 180 micrograms to about 250 micrograms per week or preferably about 150 micrograms to about 180 micrograms per week or most preferably about 180 micrograms per week.or alternatively the effective amount is in the range of about 50 micrograms to about 500 micrograms once a week("QW"), preferably about 150 micrograms to about 250 micrograms QW, or preferably about 180 micrograms to about 250 micrograms QW or preferably about 150 micrograms to about 180 micrograms QW or most preferably about 180 micrograms QW or alternatively the effective amount is in the range of about 25 micrograms to about 250 micrograms twice a week ("BIW"), preferably about 75 micrograms to about 125 micrograms BIW, preferably about 75 micrograms to about 125 micrograms BIW, or preferably about 75 micrograms to about 90 micrograms BIW, or most preferably about 90 micrograms BIW When the pegylated interferon-alfa administered to a pediatric patient is a pegylated interferon alfa-2a, the therapeutically effective amount of pegylated interferon alfa-2a administered during the treatment in accordance with the present invention, including in first treatment time period is in the range of about 50 micrograms to about 500 micrograms once a week("QW"), preferably about 300 micrograms to about 375 micrograms QW or the therapeutically effective amount of pegylated interferon alfa-2a administered to a pediatric patient is in the range of about 50 micrograms to about 250 micrograms twice a week, preferably about 150 micrograms to about 190 micrograms once a week Ribavirin is administered to the patient in association with pegylated interferon-alfa, that is, before, after or concurrently with the administration of the pegylated interferon alfa. The pegylated interferon-alfa dose is preferably administered during the same period of time that the patient receives doses of ribavirin. The amount of ribavirin administered concurrently with the pegylated interferon-alfa is from about 400 to about 1600 mg per day, preferably about 600 to about 1200 mg/day or about 800 to about 1200 mg day and most preferably about 1000 to about 1200 mg/kg a day. The pegylated interferon-alfa dose is also preferably administered to the pediatric patient during the same period of time that such patient receives doses of ribavirin. The amount of ribavirin administered to the pediatric patient concurrently with the pegylated interferon-alfa is from about 8 to about 15 mg per kilogram per day, preferrably about 8, 12 or 15 mg per kilogram per day, in divided doses.

Pegylated interferon-alfa formulations are not effective when administered orally, so the preferred method of administering the pegylated interferon-alfa is parenterally, preferably by subcutaneous, IV, or IM, injection. Ribavirin may be administered orally in capsule, tablet or liquid form in association with the parenteral administration of pegylated interferon-alfa. Of course, other types of administration of both medicaments, as they become available are contemplated, such as by nasal spray, transdermally, by suppository, by sustained release dosage form, and by pulmonary inhalation. Any form of administration will work so long as the proper dosages are delivered without destroying the active ingredient.

The term "nucleoside and nucleotide reverse transcriptase inhibitors" ("NTRI"s) as used herein means nucleosides and nucleotides and analogues thereof that inhibit the activity of HIV-1 reverse transcriptase, the enzyme which catalyzes the conversion of viral genomic HIV-1 RNA into proviral HIV-1 DNA.

Typical suitable NRTIs include zidovudine (AZT) available under the RETROVIR tradename from Glaxo-Wellcome Inc., Research Triangle, N.C. 27709; didanosine (ddI) available under the VIDEX tradename from Bristol-Myers Squibb Co., Princeton, N.J. 08543; zalcitabine (ddC) available under the HIVID tradename from Roche Pharmaceuticals, Nutley, N.J. 07110; stavudine (d4T) available under the ZERIT trademark from Bristol-Myers Squibb Co., Princeton, N.J. 08543; Iamivudine (3TC) available under the EPIVIR tradename from Glaxo-Wellcome Research Triangle, N.C. 27709; abacavir (1592U89) disclosed in WO96/30025 and available under the ZIAGEN tradename from Glaxo-Wellcome Research Triangle, N.C. 27709; adefovir dipivoxil [bis(POM)-PMEA] available under the PREVON tradename from Gilead Sciences, Foster City, Calif. 94404; lobucavir (BMS-180194), a nucleoside reverse transcriptase inhibitor disclosed in EP-0358154 and EP-0736533 and under development by Bristol-Myers Squibb, Princeton, N.J. 08543; BCH-10652, a reverse transcriptase inhibitor (in the form of a racemic mixture of BCH-10618 and BCH-10619) under development by Biochem Pharma, Laval, Quebec H7V, 4A7, Canada; emitricitabine [(−)-FTC] licensed from Emory University under Emory Univ. U.S. Pat. No. 5,814,639 and under development by Triangle Pharmaceuticals, Durham, N.C. 27707; beta-L-FD4(also called beta-L-D4C and named beta-L-2', 3'-dideoxy-5-fluorocytidene) licensed by Yale University to Vion Pharmaceuticals, New Haven Conn. 06511; and DAPD, the purine nucleoside, (−)-beta-D-2,6,-diaminopurine dioxolane disclosed in EP 0656778 and licensed by Emory University and the University of Georgia to Triangle Pharmaceuticals, Durham, N.C. 27707; and Iodenosine (FddA), 9-(2,3-dideoxy-2-fluoro-b-D-threo-pentofuranosyl)adenine, a acid stable purine-based reverse transcriptase inhibitor discovered by the NIH and under development by U.S. Bioscience Inc., West Conshohoken, Pa. 19428.

The term "non-nucleoside reverse transcriptase inhibitors" ("NNRTI" s) as used herein means non-nucleosides that inhibit the activity of HIV-1 reverse transcriptase.

Typical suitable non-nucleoside reverse transcriptase inhibitors include nevirapine (BI-RG-587) available under the VIRAMUNE tradename from Boehringer Ingelheim, the manufacturer for Roxane Laboratories, Columbus, Ohio 43216; delaviradine (BHAP, U-90152) available under the RESCRIPTOR tradename from Pharmacia & Upjohn Co., Bridgewater N.J. 08807; efavirenz (DMP-266) a benzoxazin-2-one disclosed in WO94/03440 and available under the SUSTIVA tradename from DuPont Pharmaceutical Co., Wilmington, Del. 19880-0723; DuPont 961 and DuPont 083 also under development by DuPont Pharmaceutical Co., Wilmington, Del. 19880-0723; PNU-142721, a furopyridine-thiopyrimide under development by Pharmacia and Upjohn, Bridgewater N.J. 08807; capravirine(formerly AG-1549 or Shionogi # S-1153); 5-(3,5-dichlorophenyl)-thio-4-isopropyl-1-(4-pyridyl)methyl-IH-imidazol-2-ylmethyl carbonate disclosed in WO 96/10019 and under clinical development by Agouron Pharmaceuticals, Inc., LaJolla Calif. 92037-1020; MKC-442 1-(ethoxymethyl)-5-(1-methylethyl)-6-(phenylmethyl)-(2,4(1H,3H)-pyrimidinedione discovered by Mitsubishi Chemical Co. and under development by Triangle Pharmaceuticals, Durham, N.C. 27707; and (+)-calanolide A (NSC-675451) and B coumarin derivatives disclosed in NIH U.S. Pat. No. 5,489,697, licensed to Med Chem Research, which is co-developing (+) calanolide A with Vita-invest as an orally administrable product.

The term "protease inhibitor" ("PI") as used herein means inhibitors of the HIV-1 protease, an enzyme required for the proteolytic cleavage of viral polyprotein precursors (e.g., viral GAG and GAG Pol polyproteins), into the individual functional proteins found in infectious HIV-1. HIV protease inhibitors include compounds having a peptidomimetic structure, high molecular weight (7600 daltons) and substantial peptide character, e.g. CRIXIVAN (available from Merck) as well as nonpeptide protease inhibitors e.g., VIRACEPT (available from Agouron).

Typical suitable protease inhibitors include saquinavir (Ro 31-8959) available in hard gel capsules under the INVIRASE tradename and as soft gel capsules under the FORTOUASE tradename from Roche Pharmaceuticals, Nutley, N.J. 07110-1199; ritonavir (ABT-538) available under the NORVIR tradename from Abbott Laboratories, Abbott Park, Ill. 60064; indinavir (MK-639) available under the CRIXIVAN tradename from Merck & Co., Inc., West Point, Pa. 19486-0004; MK-994, under development by Merck & Co., Inc., West Point, Pa. 19486-0004; nelfnavir (AG-1343) available under the VIRACEPT tradename from Agouron Pharmaceuticals, Inc., LaJolla, Calif. 92037-1020; Ag 1776 under development by Agouron Pharmaceuticals, Inc., LaJolla, Calif. 92037-1020; amprenavir (141W94), a non-peptide protease inhibitor, tradename AGENERASE, under development by Vertex Pharmaceuticals, Inc., Cambridge, Mass. 02139-4211 and available from Glaxo-Wellcome, Research Triangle, N.C. under an expanded access program; lasinavir (BMS-234475) available from Bristol-Myers Squibb, Princeton, N.J. 08543 (originally discovered by Novartis, Basel, Switzerland (CGP-61755); DMP-450, a cyclic urea discovered by Dupont and under development by Triangle Pharmaceuticals; BMS-2322632, PD 178390 under development by Pake-Davis. Morris Plains, N.J. 07050; an azapeptide under development by Bristol-Myers Squibb, Princeton, N.J. 08543 as a 2nd-generation HIV-1 PI; and ABT-378 under development by Abbott, Abbott Park, Ill. 60064; and AG-1549 an orally active imidazole carbamate discovered by Shionogi (Shionogi #S-1153) and under development by Agouron Pharmaceuticals, Inc., LaJolla Calif. 92037-1020.

The term "anti-HIV-1 therapy" as used herein means any anti-HIV-1 drug found useful for treating HIV-1 infections in man alone, or as part of multidrug combination therapies, especially the triple and quadruple combination therapies called HAART.

Typical suitable anti-HIV-1 therapies include, but are not limited to multidrug combination therapies such as (i) at least three anti-HIV-1 drugs selected from two NRTIs, one PI, a second PI, and one NNRTI; and (ii) at least two anti-HIV-1 drugs selected from, NNRTIs and PIs; see Tables I, II and III, hereinafter.

Typical suitable HAART—multidrug combination therapies—include (a) triple combination therapies such as two NRTIs and one PI; or (b) two NRTIs and one NNRTI; and (c) quadruple combination therapies such as two NRTIs, one PI and a second PI or one NNRTI. In treatment-naive patients, it is preferred to start anti-HIV-1 treatment with the triple combination therapy; the use of two NRTIs and one PI is prefered unless there is intolerance to PIs. Drug compliance is essential. The CD4+ and HIV-1-RNA plasma levels should be monitored every 3-6 months. Should viral load plateau, a fourth drug, e.g., one PI or one NNRTI could be added. See the Table A hereinbelow.

TABLE A

ANTI-HIV-1 MULTI DRUG COMBINATION THERAPIES

A. Triple Combination Therapies

1. Two NRTIs[1] + one PI[2]
2. Two NRTIs[1] + one NNRTI[3]

B. Quadruple Combination Therapies[4]

Two NRTIs + one PI + a second PI or one NNRTI

TABLE A-continued

ANTI-HIV-1 MULTI DRUG COMBINATION THERAPIES

C. ALTERNATIVES:[5]

Two NTRI[1]
One NTRI[5] + one PI[2]
Two PIs[6] ± one NTRI[7] or NNRTI[3]
One PI[2] + one NRTI[7] + one NNRTI[3]

FOOTNOTES TO TABLE A
[1]One of the following: zidovudine + lamivudine; zidovudine + didanosine; stavudine + lamivudine; stavudine + didanosine; zidovudine + zalcitabine; See also Table I
[2]Indinavir, nelfinavir, ritonavir or saquinavir soft gel capsules. Ritonavir is used less frequently because of troublesome adverse effects. The old formulation of saquinavir was used least often because of its poor bioavailability and limited effectiveness, but the new saquinavir formulation should be more effective. See also Table III.
[3]Nevirapine or delavirdine. See also Table II
[4]See A-M. Vandamme et al Antiviral Chemistry + Chemotherapy 9:187 at p 193–197 and FIGS. 1 + 2.
[5]Alternative regimens are for patients unable to take a recommended regimen because of compliance problems or toxicity, and for those who fail or relapse on a recommended regimen. Double nucleoside combinations may lead to HIV- resistance and clinical failure in many patients.
[6]Most data obtained with saquinavir and ritonavir (each 400 mg bid). See also Table III
[7]Zidovudine, stavudine or didanosine. See also Table I Other anti-HIV-1 drugs useful for administration in association with pegylated interferon alfa include hydroxyurea, ribavirin, IL-2 and IL-12, and Yissum Project No. 11607. These above-listed anti-HIV-1 drugs may also be administered in association with pegylated interferon alfa in association with any anti-HIV-1 drug therapy, especially the triple and quadruple drug combinations called HAART.

Hydroxyurea (Droxia) is a ribonucleoside triphosphate reductase inhibitor, the enzyme involved in the activation of T-cells. Hydroxyurea discovered at the NCl is under development by Bristol-Myers Squibb. In preclinical studies, it was shown to have a synergistic effect on the activity of didanosine and has been studied with stavudine.

Yissum Project No. 11607, a synthetic protein based on the HIV-1 Vif protein under preclinical development by Yissum Research Development Co., Jerusalem 91042, Israel.

IL-2 is disclosed in Ajinomoto EP-0142268, Takeda EP-0176299, and Chiron U.S. Pat. Nos. RE 33653, 4,530,787, 4,569,790, 4,604,377, 4,748,234, 4,752,585, and 4,949,314 is available under the PROLEUKIN(aldesleukin) tradename from Chiron Corp., Emeryville, Calif. 94608-2997 as a lyophilized powder for IV infusion or sc administration upon reconstitution and dilution with water; doses of about 1 to about 20 million IU/day, sc is preferred; a dose of about 15 million IU/day, sc is more preferred.

IL-12 is disclosed in WO96/25171 and is available from Roche Pharmaceuticals, Nutley, N.J. 07110-1199 and American Home Products, Madison, N.J. 07940; a dose of about 0.5 microgram/kg/day to about 10 microgram/kg/day, sc.

Pentafuside (DP-178, T-20) a 36-amino acid synthetic peptide, disclosed in U.S. Pat. No. 5,464,933 licensed from Duke University to Trimeris which is developing pentafuside in collaboration with Duke University; pentafuside acts by inhibiting fusion of HIV-1 to target membranes. Pentafuside (3-100 mg/day) is given as a continuous sc infusion or injection together with efavirenz and 2 PI's to HIV-1 positive patients refractory to a triple combination therapy; use of 100 mg/day is preferred. A second generation fusion inhibitor T-1249 (39 aa) is under development by Trimeris.

Other inhibitors under development include CXCR4, AM03100, and INTERGRASE by Merck & Co.

Ribavirin, 1-β-D-ribofuranosyl-1H-1,2,4-triazole-3-carboxamide, available from ICN Pharmaceuticals, Inc., Costa Mesa, Calif., is described in the Merck Index, compound No. 8199, Eleventh Edition. Its manufacture and formulation is described in U.S. Pat. No. 4,211,771.

The pegylated inteferon alfa, $PEG_{12000}$-IFN-alfa2b(available from Schering-Plough Research Institute, Kenilworth, N.J.) increased the in vitro anti HIV-1 activity of ribavirin. The combination of $PEG_{12000}$-IFN-alfa2b and ribavirin inhibited HIV replication in vitro using phytohemagylutinin ("PHA"-P)—activated peripheral blood mononuclear cells ("PBMCs") at doses corresponding to plasmatic concentrations observed in animals and man. Healthy PBMCs were separated from a buffy-coat of one HIV-seronegative blood donor by Ficoll-Hypaque density gradient centrifugation. PBMCs were activated by 1 µg/ml phytohemagglutinin (PHA-P) for two days in cell culture medium A: RPMI 1640 supplemented with 10% heat-inactivated (+56° C., 45 min.) fetal calf plasma (FCS), 2 mM L-glutamine and a tri-antibiotic mixture (penicillin, streptomycin, neomycin; PSN). After these two days, cells were washed and cultured at one million cell per milliliter in cell culture medium B: cell culture medium A supplemented with 20 IU/ml recombinant human interleukin-2. Cells were maintained at +37° C. in a 5% $CO_2$-air humidified atmosphere. Experiments were repeated twice with cells of other blood donors. In total, three independent experiments were performed.

PBMCs were infected with 1,000 50% Tissue Culture Infectious Doses (TCID50) of the reference HIV-1-LAI strain [F. Barré-Sinoussi, Science, 1983, 220, 868-871]. This strain has been amplified using PHA-P-activated umbilical blood mononuclear cells (UBMC). Viral stock has been then titrated on PHA-P activated PBMC by end-point dilution. TCID50 was then calculated using Karber's formula [Arch. Exp. Path. Pharmak., 1931, 162, 126-133].

$PEG_{12000}$-IFN-α2b and ribavirin, alone and in combination, and AZT used as a control, were administrated 24 hours before HIV-1 infection and maintained all along the culture. Three doses of $PEG_{12000}$-IFN-α2b and ribavirin were used.

200,000 PHA-P-activated PBMCs were added to each well of 96-well microplates. Cells were 24 hour-pretreated prior to infection with the reference HIV-1-LAI strain. Twice a week, cell supernatants were collected, and drugs and medium were renewed. At day 7, RT activity were determined in cell supernatants, and potential cytotoxic effects of drugs and drug combinations were evaluated by microscopic observation.

Viral replication was measured by determining reverse transcriptase ("RT") activity in cell supernatants using Retro-Sys® kit, according to manufacturer's recommendations (Innovagen, Lund, Sweden).

Effective doses were calculated using cumulative RT activities with Chou J. and TC. microcomputer software.

The combined effects were analyzed using either the combination index (CI) [Chou & Talalay, 1984] with J and T C Chou microcomputer software, or the fractionary inhibitory concentration (FIC) index [Antimicrob. Agents. Chemother., 1987, 31, 1613-1617]. When the CI or FIC index is equal to 1, the combination is additive. When it is below 1.0, the combination is synergistic, and when it is above 1.0, the combination is judged as antagonistic.

$PEG_{12000}$-IFN-alfa2b as well as the combination of $PEG_{12000}$-IFN-alfa2b and ribavirin inhibited the HIV replication at doses corresponding to plasmatic concentrations measured in mice and HIV-1 infected patients [B E. Gilbert, et al. Antimicrob. Agents Chemother., 1988, 32.117-121; E. Connor at al., Antimicrob. Agents Chemother., 1993, 37, 537-539].

These above-listed anti-HIV-1 drugs may also be administered in association with pegylated interferon alfa in association with any anti-HIV-1 drug therapy, especially the triple and quadruple drug combinations called HAART.

The term "interferon-alfa" as used herein means the family of highly homologous species-specific proteins that inhibit viral replication and cellular proliferation and modulate immune response. Typical suitable interferon-alfas include, but are not limited to, recombinant interferon alfa-2b such as Intron-A interferon available from Schering Corporation, Kenilworth, N.J., recombinant interferon alfa-2a such as Roferon interferon available from Hoffmann-La Roche, Nutley, N.J., recombinant interferon alpha-2C such as Berofor alpha 2 interferon available from Boehringer Ingelheim Pharmaceutical, Inc., Ridgefield, Conn., interferon alpha-n1, a purified blend of natural alfa interferons such as Sumiferon available from Sumitomo, Japan or as Wellferon interferon alpha-n1 (INS) available from the Glaxo-Wellcome Ltd., London, Great Britain, or a consensus alpha interferon such as those described in U.S. Pat. Nos. 4,897,471 and 4,695,623 (especially Examples 7, 8 or 9 thereof) and the specific product available from Amgen, Inc., Newbury Park, Calif., or interferon alfa-n3 a mixture of natural alfa interferons made by Interferon Sciences and available from the Purdue Frederick Co., Norwalk, Conn., under the Alferon Tradename. The use of interferon alfa-2a or alpha 2b is preferred. Since interferon alpha 2b, among all interferons, has the broadest approval throughout the world for treating chronic hepatitis C infection, it is most preferred. The manufacture of interferon alpha 2b is described in U.S. Pat. No. 4,530,901.

The term "pegylated interferon alfa" as used herein means polyethylene glycol modified conjugates of interferon alfa, preferably interferon alfa-2a and -2b. The preferred polyethylene-glycol-interferon alfa -2b conjugate is $PEG_{12000}$-interferon alfa 2b. The phrases "12,000 molecular weight polyethylene glycol conjugated interferon alpha" and "$PEG_{12000}$-IFN alfa" as used herein mean conjugates such as are prepared according to the methods of International Application No. WO 95/13090 and containing urethane linkages between the interferon alfa-2a or -2b amino groups and polyethylene glycol having an average molecular weight of 12000.

The preferred $PEG_{12000}$-interferon alfa-2b is prepared by attaching a PEG polymer to the epsilon amino group of a lysine residue in the IFN alfa-2b molecule. A single $PEG_{12000}$ molecule is conjugated to free amino groups on an IFN alfa-2b molecule via a urethane linkage. This conjugate is characterized by the molecular weight of $PEG_{12000}$ attached. The PEG12000-IFN alfa-2b conjugate is formulated as a lyophilized powder for injection. The objective of conjugation of IFN alfa with PEG is to improve the delivery of the protein by significantly prolonging its plasma half-life, and thereby provide protracted activity of IFN alfa.

Other interferon alfa conjugates can be prepared by coupling an interferon alfa to a water-soluble polymer. A non-limiting list of such polymers include other polyalkylene oxide homopolymers such as polypropylene glycols, polyoxyethylenated polyols, copolymers thereof and block copolymers thereof. As an alternative to polyalkylene oxide-based polymers, effectively non-antigenic materials such as dextran, polyvinylpyrrolidones, polyacrylamides, polyvinyl alcohols, carbohydrate-based polymers and the like can be used. Such interferon alfa-polymer conjugates are described in U.S. Pat. No. 4,766,106, 4,917,888, European Patent Application No. 0 236 987, European Patent Application Nos. 0510 356, 0 593 868 and 0 809 996 (pegylated interferon alfa-2a) and International Publication No. WO 95/13090.

Pharmaceutical composition of pegylated interferon alfa-suitable for parenteral administration may be formulated with a suitable buffer, e.g., Tris-HCl, acetate or phosphate such as dibasic sodium phosphate/monobasic sodium phosphate buffer, and pharmaceutically acceptable excipients (e.g., sucrose), carriers (e.g. human plasma albumin), toxicity agents (e.g. NaCl), preservatives (e.g. thimerosol, cresol or benylalcohol), and surfactants(e.g. tween or polysorabates) in sterile wafer for injection. The pegylated interferon alfa-may be stored as lyophilized powders under a refrigeration at 2°-8° C. The reconstituted aqueous solutions are stable when stored between 2° and 8° C. and used within 24 hours of reconstitution. See for example U.S. Pat. Nos, 4,492,537; 5,762,923 and 5,766,582. The reconstituted aqueous solutions may also be stored in prefilled, multi-dose syringes such as those useful for delivery of drugs such as insulin. Typical suitable syringes include systems comprising a prefilled vial attached to a pen-type syringe such as the NOVOLET Novo Pen available from Novo Nordisk, as well as prefilled, pen-type syringes which allow easy self-injection by the user. Other syringe systems include a pen-type syringe comprising a glass cartridge containing a diluent and lyophilized pegylated interferon alfa powder in a separate compartment.

Certain CCR5 antagonist compounds represented by the structural formula I or II or III or IV may exist in different isomeric (e.g., enantiomers, diastereoisomers and atropisomers) forms. The invention contemplates all such isomers both in pure form and in admixture, including racemic mixtures.

Certain compounds of formulas I or II or III or IV will be acidic in nature, e.g. those compounds which possess a carboxyl or phenolic hydroxyl group. These compounds may form pharmaceutically acceptable salts. Examples of such salts may include sodium, potassium, calcium, aluminum, gold and silver salts. Also contemplated are salts formed with pharmaceutically acceptable amines such as ammonia, alkyl amines, hydroxyalkylamines, N-methylglucamine and the like.

Certain basic compounds of formulas I or III or IV also form pharmaceutically acceptable salts, e.g., acid addition salts. For example, the pyrido-nitrogen atoms may form salts with strong acid, while compounds having basic substituents such as amino groups also form salts with weaker acids. Examples of suitable acids for salt formation are hydrochloric, sulfuric, phosphoric, acetic, citric, oxalic, malonic, salicylic, malic, fumaric, succinic, ascorbic, maleic, methanesulfonic and other mineral and carboxylic acids well known to those in the art. The salts are prepared by contacting the free base form with a sufficient amount of the desired acid to produce a salt in the conventional manner. The free base forms may be regenerated by treating the salt with a suitable dilute aqueous base solution such as dilute aqueous NaOH, potassium carbonate, ammonia and sodium bicarbonate. The free base forms differ from their respective salt forms somewhat in certain physical properties, such as solubility in polar solvents, but the acid and base salts are otherwise equivalent to their respective free base forms for purposes of the invention.

All such acid and base salts are intended to be pharmaceutically acceptable salts within the scope of the invention and all acid and base salts are considered equivalent to the free forms of the corresponding compounds of formulas I or II for purposes of the invention.

Compounds of the formula I or II or III or IV are the invention of other inventive entities. Compounds of the formula I or II are disclosed, together with methods of making them, in commonly-owned U.S. patent application Ser. No. 09/562,815, filed May 1, 2000 and now U.S. Pat. No. 6,387,930 and compounds of the formula or III or IV in commonly-owned U.S. patent application Ser. No. 09/562,814, filed May 1, 2000, and now U.S. Pat. No. 6,391,865, each of which were filed on the same date as this application, both of which are hereby incorporated by reference Compounds of formulas I or II or II or IV can be also made by the procedures known in the art, for example by the procedures described in the following reaction schemes, by the methods described in the examples below, and by using the methods described in WO96/26196, WO98/05292, WO98/10425 and WO98/06697.

For preparing pharmaceutical compositions from the compounds of formula I or II or III or IV, inert, pharmaceutically acceptable carriers can be either solid or liquid. Solid form preparations include powders, tablets, dispersible granules, capsules, cachets and suppositories. The powders and tablets may be comprised of from about 5 to about 95 percent active ingredient. Suitable solid carriers are known in the art, e.g. magnesium carbonate, magnesium stearate, talc, sugar or lactose. Tablets, powders, cachets and capsules can be used as solid dosage forms suitable for oral administration. Examples of pharmaceutically acceptable carriers and methods of manufacture for various compositions may be found in A. Gennaro (ed.), Remington's Pharmaceutical Sciences, 18th Edition, (1990), Mack Publishing Co., Easton, Pa.

Liquid form preparations include solutions, suspensions and emulsions. As an example may be mentioned water or water-propylene glycol solutions for parenteral injection or addition of sweeteners and opacifiers for oral solutions, suspensions and emulsions. Liquid form preparations may also include solutions for intranasal administration.

Aerosol preparations suitable for inhalation may include solutions and solids in powder form, which may be in combination with a pharmaceutically acceptable carrier, such as an inert compressed gas, e.g. nitrogen.

Also included are solid form preparations which are intended to be converted, shortly before use, to liquid form preparations for either oral or parenteral administration. Such liquid forms include solutions, suspensions and emulsions.

The compounds of formula I or II or III or IV may also be deliverable transdermally. The transdermal compositions can take the form of creams, lotions, aerosols and/or emulsions and can be included in a transdermal patch of the matrix or reservoir type as are conventional in the art for this purpose.

Preferably the compounds of formula I or II or III or IV is administered orally.

Preferably, the pharmaceutical preparation is in a unit dosage form. In such form, the preparation is subdivided into suitably sized unit doses containing appropriate quantities of the active component, e.g., an effective amount to achieve the desired purpose.

The quantity of active compound of formula I or II or III or IV in a unit dose of preparation may be varied or adjusted from about 10 mg to about 500 mg, preferably from about 25 mg to about 300 mg, more preferably from about 50 mg to about 250 mg, and most preferably from about 55 mg to about 200 mg, according to the particular application.

The actual dosage employed may be varied depending upon the requirements of the patient and the severity of the condition being treated. Determination of the proper dosage regimen for a particular situation is within the skill of the art. For convenience, the total daily dosage may be divided and administered in portions during the day as required.

The amount and frequency of administration of the compounds of formula I or III or IV and/or the pharmaceutically acceptable salts thereof will be regulated according to the judgment of the attending clinician considering such factors as age, condition and size of the patient as well as severity of the symptoms being treated. A typical recommended daily dosage regimen for oral administration of the compounds of formula I or II or III or IV can range from about 100 mg/day to about 300 mg/day, preferably 150 mg/day to 250 mg/day, more preferably about 200 mg/day, in two to four divided doses.

A person suffering from chronic hepatitis C infection may exhibit one or more of the following signs or symptoms:
(a) elevated ALT,
(b) positive test for anti-HCV antibodies,
(c) presence of HCV as demonstrated by a positive test for the presence of HCV-RNA in the serum,
(d) clinical stigmata of chronic liver disease,
(e) hepatocelluar damage.

In a prefered aspect of the present invention, a therapeutically effective amount of the combination therapy of pegylated interferon-alfa and a CCR5 antagonist compound represented by structural formula I or II or II or IV is administered in association with a therapeutically effective amount of ribavirin and anti-retroviral therapy,e.g., HAART, to the patient having HIV-1 infection and exhibiting one or more of the above signs or symptoms in the first and second treatment time periods in amounts sufficient to eliminate or at least alleviate one or more of the signs or symptoms., and to lower the HCV-RNA plasma levels by at least a power of ten, and preferably to eradicate detectable HCV-RNA at least by the end of the second treatment time period and to maintain no detectable HCV-RNA for at least 24 weeks after the end of the second treatment time period. The sum of the first and second treatment time periods is about 40-50 weeks, and preferrably is 48 weeks. Administration of the ribavirin may be discontinued after the end of the second time period depending upon the judgment of the attending clinician.

The term "no detectable HCV-RNA" in the context of the present invention means that there are fewer than 100 copies of HCV-RNA per ml of plasma of the patient as measured by quantitative, multi-cycle reverse transcriptase PCR methodology. HCV-RNA is preferably measured in the present invention by research-based RT-PCR methodology well known to the skilled clinician. This methodology is referred to herein as HCV-RNA/qPCR. The lower limit of detection of HCV-RNA is 100 copies/mL. Serum HCV-RNA/qPCR testing and HCV genotype testing will be performed by a central laboratory. See also J. G. McHutchinson et al. (N. Engl. J. Med., 1998, 339:1485-1492), and G. L. Davis et al. (N. Engl. J. Med. 339:1493-1499).

In a preferred embodiment of the present invention, those patients co-infected with HIV-1 and HCV infections are treated with a combination therapy of pegylated interferon alfa and a CCR5 antagonist compound represented by structural formula I or II or III or IV in association with ribavirin and a HAART combination considered appropriate by the attending clinician and the patient; use of the interferon alfa-2b-ribavirin combination therapy sold by Schering Corp. under the REBETRON tradename is preferred.

See also J. G. McHutchinson et al. (N. Engl. J. Med., 1998, 339:1485-1492), and G. L. Davis et al. (N. Engl. J. Med. 339:1493-1499). Ribavirin, 1-β-D-ribofuranosyl-1H-1,2,4-triazole-3-carboxamide, available from ICN Pharmaceuticals, Inc., Costa Mesa, Calif., is described in the Merck Index, compound No. 8199, Eleventh Edition. Its manufacture and formulation is described in U.S. Pat. No. 4,211,771.

For the pediatric patient co-infected with the HIV-1 and HCV infections, a suitable HAART includes a NRTI+ a PI, e.g., Nelfinavir +a NNRTI, e.g., Efavirenz in combination with the dosages and dosage regimens for pegylated interferon alfa and ribavirin listed herein above. See also Tables I-IV herein below. A human growth hormone such as the polypeptide hormone, somatropin, of recombinant rDNA origin, available under the HUMATROPE tradename from Eli Lilly & Co., Indianapolis, Ind. 46285, may be administered to these pediatric patients in the dosage and administration schedule listed in the product information sheet in consultation with the attending clinician to reduce retardation of growth associated with pegylated interferon alfa treatment.

HAART is administered to the patient in association with pegylated interferon-alfa, that is, the pegylated interferon-alfa dose may be administered before, after or during the same period of time that the patient receives doses of HAART. A human growth hormone such as the polypeptide hormone, somatropin, of recombinant rDNA origin, available under the HUMATROPE tradename from Eli Lilly & Co., Indianapolis, Ind. 46285, may also be administered—in association with HAART and pegylated interferon alfa- to the pediatric patient having HIV-1 infection in the dosage and administration schedule listed in the product information sheet in consultation with the attending clinician.

In a preferred embodiment of the present invention, pegylated interferon alfa is administered to HIV-1 infected patients prior to initiation of a CCR5 antagonist compound represented by structural formula I or II or III or IV and of HAART, and preferably about two to about four weeks prior to initiation of HAART. In another preferred embodiment of the present invention, administeration of pegylated interferon alfa is initiated concurrently, i.e., on the same day with the administeration of a CCR5 antagonist compound represented by structural formula I or II or III or IV and HAART. In another preferred embodiment of the present invention the pegylated interferon-alfa is administered after the HIV-1 infected patient has initiated use of a CCR5 antagonist compound represented by structural formula I or II or III or IV and HAART.

The goal of the HIV-1 therapy of the present invention is to reduce the HIV-1-RNA viral load below the detectable limit. The "detectable limit of HIV-1-RNA" in the context of the present invention means that there are fewer than about 200 to fewer than about 50 copies of HIV-1-RNA per ml of plasma of the patient as measured by quantitative, multi-cycle reverse transcriptase PCR methodology. HIV-1-RNA is preferably measured in the present invention by the methodology of Amplicor-1 Monitor 1.5 (available from Roche Diagnsotics)or of Nuclisens HIV-1 QT-1. This methodology is described by Schooley, RT, Antiviral Therapy (1997), 2 (Suppl. 4):59-70.

The doses and dosage regimen of the NRTIs, NNRTIs, PI, pentafuside, IL-2, IL-12, a CCR5 antagonist compound represented by structural formula I or II or III or IV and pegylated interferon alfa will be determined by attending clinician in view of the approved doses and dosage regimen in the package insert or as set forth in the protocol taking into consideration the age, sex and condition of the patient and the severity of the HIV-1 and HCV infections. For the pediatric patient infected with the HIV-1, or co-infected with the HIV-1 and HCV infections a suitable HAART includes a NRTI+ a PI, e.g., Nelfinavir +a NNRTI, e.g., Efavirenz in combination with the dosages and dosage regimens for pegylated interferon alfa and ribavirin listed herein above. See also Tables I-IV hereinafter for dosages and dosage regimens.

The following clinical protocol may be used to administer the anti-HIV-1 therapy of the present invention. Many modifications of this clinical protocol will be obvious to the skilled clinician, and the following Study Design should not be interpreted as limiting the scope of the method of this invention which is only limited by the claims listed hereinafter. See for example J. G. McHutchinson et al. (N. Engl. J. Med., 1998, 339:1485-1492), and G. L. Davis et al. (N. Engl. J. Med. 339:1493-1499).

The study population should include male and female patients diagnosed with HIV-1 infection who are either treatment naive or treatment-experienced and should be included if they meet the following inclusion and exclusion criteria:

Subject Inclusion Criteria:
  Subjects diagnosed with HIV-1 infection who are either treatment naive or treatment-experienced.
  HIV-RNA by Amplicor test, Version 1.5 of greater than 500 copies/mL.
  $CD_4^+$ count greater than 100 copies/ml, preferably greater than 200 cells/mL.
  Subjects in good physical health with clinically acceptable safety laboratory test results and ECG.
  The following laboratory parameters must be met:
  Platelet count·100,00/mL
  Hemoglobin·9 gm/dL (90 gm/L)
  Absolute neutrophil count·1500/μL
  Creatinine<1.5 times the upper limit of normal
  SGOT/SGPT≦5× upper limit of normal
  Bilirubin≦2.5× upper limit of normal
  A negative urine pregnancy test (females only)

Subjects must be willing and able to give written informed consent and be able to adhere to the schedule set forth in the protocol Subject Exclusion Criteria
  Females who are breast-feeding or pregnant or who are not using adequate birth control.
  Subject with allergy to *E. coli* proteins
  Subjects with a significant past medical/psychiatric history, specifically depression or dementia.

The subjects will be randomized to receive pegylated interferon alfa 2b, i.e., $PEG_{12000}$-interferon alfa 2b at doses between 0.5 and 4.5 micrograms per kilogram e.g. at doses of 0.5, 1.0, 1.5, 3.0 or 4.5 micrograms per kilogram by subcutaneous injection once a week. The amount of ribavirin administered concurrently with the pegylated interferon-alfa is from about 400 to about 1600 mg per day, preferrably about 600 to about 1200 mg/day or about 800 to about 1200 mg day and most preferably about 1000 to about 1200 mg/kg a day.

The quantity of CCR5 antagonist compound of formula I or II or III or IV in a unit dose of formulation may be varied or adjusted from about 10 mg to about 500 mg, preferably from about 25 mg to about 300 mg, more preferably from about 50 mg to about 250 mg, and most preferably from about 55 mg to about 200 mg, according to the particular application.

HAART may also be initiated before or concurrently with the administration of the pegylated interferon alfa 2b, i.e., PEG$_{12000}$-interferon alfa 2b, a CCR5 antagonist compound of formula I or II or III or IV and ribavirin.

CCR5 antagonist compounds of the following structures are representative of formulas I and II useful in the present invention:

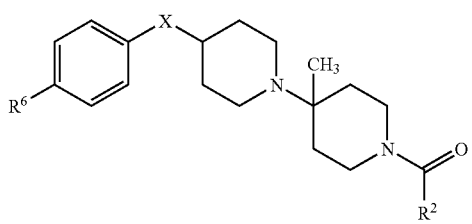

wherein $R^6$, X and $R^2$ are as defined in the following table:

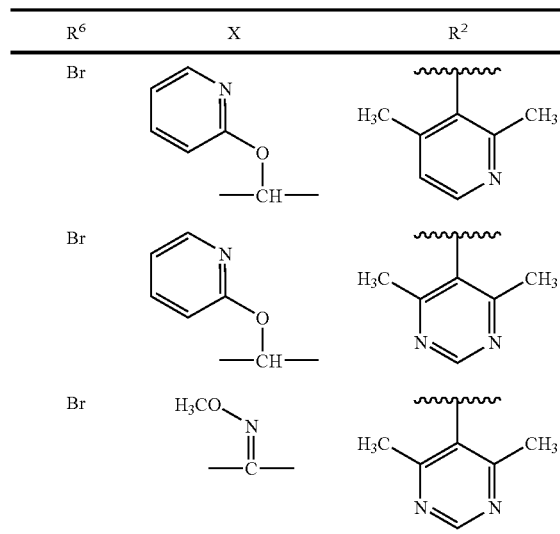

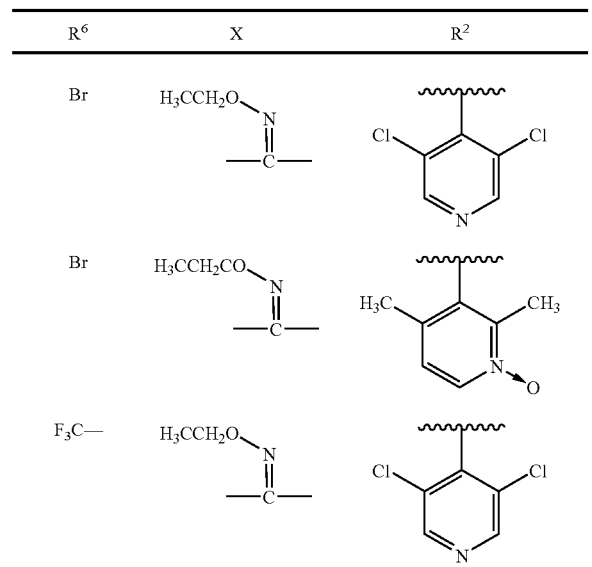

CCR5 antagonist compounds of the following structures are representative of formulas III and IV useful in the present invention:

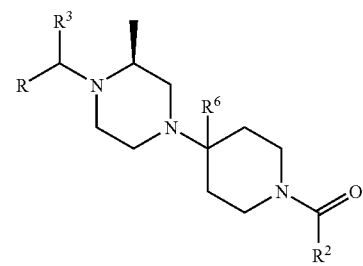

wherein R, $R^3$, $R^6$ and $R^2$ are as defined in the following table:

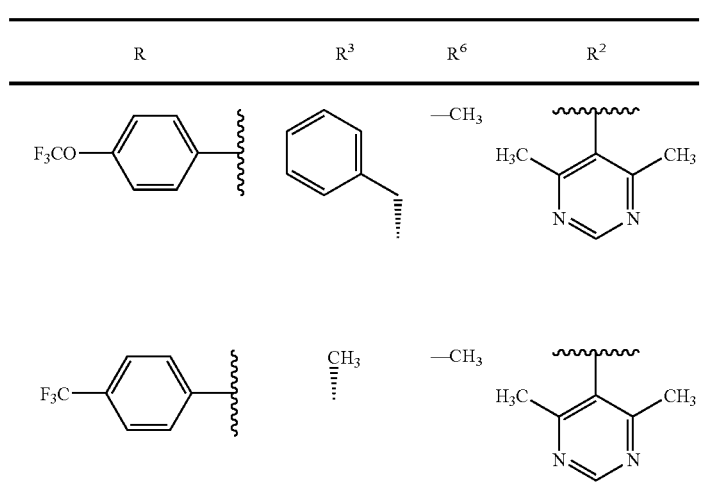

-continued

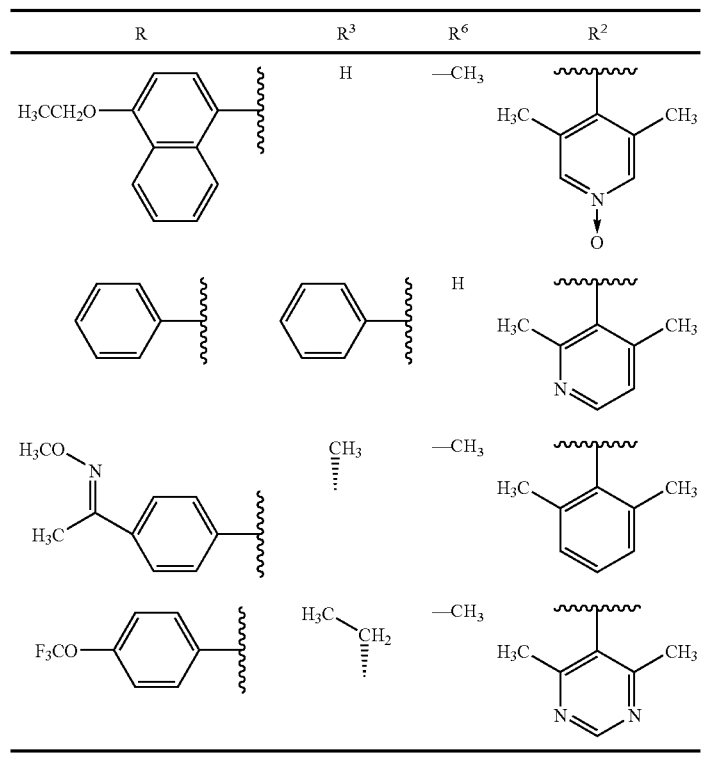

The actual dosages employed may be varied depending upon the requirements of the patient and the severity of the condition being treated. Determination of the proper dosage regimen for a particular situation is within the skill of the art. For convenience, the total daily dosage may be divided and administered in portions during the day as required.

Overall Design and Plan of the Study:

The primary efficacy objective will be lowering of the HIV-I-RNA plasma levels by a factor of 10 or greater.

Plasma HIV-1-RNA/qPCR testing will be performed by a central laboratory. A positive HIV-1-RNA assay result will be required at Baseline; only patients positive for HIV-1-RNA will be eligible to participate.

TABLE I

NUCLEOSIDE REVERSE TRANSCRIPTASE INHIBITORS (NRTI) DOSAGE & DOSAGE REGIMEN

| NRTI (Tradename, Marketer) | Usual adult dosage |
| --- | --- |
| Zidovudine, AZT (Retrovir-Glaxo Wellcome)* | 200 mg PO tid or 300 mg PO bid |
| Stavudine (Zerit-Bristol-Myers Squibb)* | 40 mg PO bid[1] |
| Didanosine (Videx-Bristol-Myers Squibb)* | 200 mg PO bid[2] |
| Lamivudine (Epivir-Glaxo Wellcome)* | 150 mg PO bid[3] |
| Zalcitabine (Hivid-Roche) | 0.75 mg PO tid |
| Zidovudine plus lamivudine (Combivir-Glaxo Wellcome) | 1 tablet PO bid[4] |
| Abacavir (Ziagen-Glaxo-Wellcome) | 200 or 400 mg PO tid |
| Adefovir dipivoxil (Prevon-Gilead Sciences) | 125 or 200 mg PO qd[5] |
| Lobucavir (BMS-180194-BMS) | 200 mg PO bid[6] |
| | 200 mg PO, qid |

TABLE I-continued

NUCLEOSIDE REVERSE TRANSCRIPTASE INHIBITORS (NRTI) DOSAGE & DOSAGE REGIMEN

| NRTI (Tradename, Marketer) | Usual adult dosage |
| --- | --- |
| BCH-10652 (Biochem Pharma) | 400 mg PO, qid[7] |
| Emitricitabine ((-)-FTC-Triangle Pharmaceuticals) | 200 mg PO qd[8] |
| Beta-L-FD4 (B-L-D4C-Vion Pharmaceutical) | 0.2–25 mg/ky/day[9] |
| DAPD (Triangle Pharmaceuticals) | —[10] |
| Lodenosine (FddA-U.S. Bioscience) | 1.6–3.2 mg/Kg PO bid[11] |

Footnotes Table I

*Available in a liquid formulation.

[1] For patients less than 60 kg, 30 mg PO bid.

[2] With tablets; for patients <60 kg. 125 mg PO bid; >60 kg. 200 mg PO bid;. With powder, dosage varies from 167 mg (<60 kg) to 250 mg PO (<60 kg) bid. Doses should be taken at least 30 minutes before meals or at least two hours afterward.

[3] For patients less than 50 kg. 2 mg/kg PO bid.

[4] Each tablet contains 300 mg of zidovudine and 150 mg of lamivudine.

[5] Available under an expanded access program-a NIH-sponsored Phase III Trial

[6] Phase II.

[7] Phase I/II; see PharmaProjects, sections J5A & J5Z.

[8] Phase II/III; see PharmaProjects, sections J5A & J5Z.

[9] Preclinical; active in duck HBV model; see PharmaProjects, sections J5A & J5Z.

[10] Preclinical; active po and IV; DAPD is a prodrug of another dioxolene purine, DXG. See PharmaProjects, sections J5A & J5Z.

[11] Phase II, FddA has potential for once-a-day dosage.

TABLE II

NON-NUCLEOSIDE REVERSE TRANSCRIPTASE INHIBITORS (NNRTI) Dosage and Dosage Regimen

| NNRTI (Tradename, Marketer) | Usual adult dosage and Dosage Regimen |
| --- | --- |
| Nevirapine (Viramune-Roxane) | 200 mg PO bid[1] |
| Delavirdine (Rescriptor-Pharmacia & Upjohn) | 400 mg PO tid |
| Efavirenz (Sustiva, Dupont) | 200 mg PO qid[2] |
| PNU-142721 (Pharmacia + Upjohn) | —[3] |
| AG-1549 (Agouvon Pharmaceuticals) | —[4] |
| MKC-442 (Triangle Pharmaceuticals) | 750 mg PO bid[5] |
| (+)-Calanolide A (Med Chem Research) | 800 mg PO[6] |

[1] For the first two weeks of treatment with nevirapine, to decrease the risk of rash, patients should take only one 200-mg tablet per day.
[2] Quadruple Therapy of efavirenz with indinavir + 2 NRTIs or Triple Therapy of efavirenz + AZT + lamivudine.
[3] Preclinical Phase; see PharmaProjects, sections J5A & J5Z
[4] Phase I/II evaluating dose and comcomitant use with other anti-HIV-1 therapies; see Pharmaprojects, sections J5A & J5Z.
[5] Triple Therapy of (a) MKC-442 with stavudine and either lamivudine or didanosine or (b) MKC-442 with nelfinavir (qv) and NRTIs.
[6] Phase I; see Pharmaprojects, sections J5A & J5Z

TABLE III

Protease Inhibitor (PI) Dosage and Dosage Regimen

| PI (Tradename, Marketer) | Dosage + Dosage Regimen |
| --- | --- |
| Saquinavir (Invirase-hard gel capsule-Roche) | 600 mg PO tid[1] |
| (Fortovase-soft gel capsule-Roche) | 1100 mg PO tid[1] |
| Ritonavir (Norvir-Abbott) | 600 mg PO bid[2] |
| Indinavir (Crixivan-Merck) | 800 mg PO qid[3] |
| Nelfinavir (Viracept-Agouron) | 750 mg PO tid[4] |
| Agenerase (Amprenavir, 141W94, Glaxo) | 900 mg–1200 mg PO bid[5] |
| Lasinavir (BMS-234475, BMS) | —[6] |
| DMP-450 (Triangle Pharmaceuticals) | —[7] |
| BMS-2322623 (BMS) | —[8] |
| ABT-378 (Abbott) | 60 mg PO bid[9] |

[1] With, or within two hours after, a full meal.
[2] With food. The liquid formulation has an unpleasant taste; the manufacturer suggests taking it with chocolate milk or a liquid nutritional supplement.
[3] With water, one hour before or two hours after a meal. Patients taking indinavir should drink at least 48 ounces (1.5 liter) of water daily.
[4] With food.
[5] Quadruple Combination Therapy of amprenavir with AZT + lamivudine + abacavir.
[6] Phase I/II; see Pharmaprojects, sections J5A & J5Z.
[7] Phase II; see Pharmaprojects, sections J5A & J5Z.
[8] Preclinical Studies; Prodrug esters of BMS 2322623 enhance oral absorption; see Pharmaprojects, sections J5A & J5Z.
[9] Phase I Studies show ABT-378 to be 10× more potent than ritonavir; see Pharmaprojects sections J5A & J5Z.

TABLE IV

Other Anti-HIV-1 Drugs

| Drug (Trade Name, Marketer) | Usual Adult Dosage and Dosage Regimen |
| --- | --- |
| Hydroxyurea (Droxia, BMS) | 1000 mg PO qid[1] |
| Ribavirin (Rebetol, Schering-Plough) | 600 mg–1200 mg/day, PO |
| IL-2 (Proleukin, Chiron Corp.) | 1–20 milliom IU/day, sc |
| IL-12 (Roche) | 0.5–10 micrograms/kg/day, sc |
| Yissum Project No. 11607 (Yissum) | —[2] |

[1] Triple Therapy of hydroxyurea with 400 mg ddI + 500 mg AZT; see PharmaProjects, section B3C1
[2] Preclinical; see Pharmaprojects, sections J5A & J5Z.

The following assays can be used to identify a compound as a CCR5 antagonist as well as to determine the CCR5 antagonistic activity of the compounds of formulas I to IV. These assays are disclosed in commonly-owned U.S. patent application Ser. No. 09/562,815 and commonly-owned U.S. patent application Ser. No. 09/562,814, filed on the same date as this application CCR5 Membrane Binding Assay:

A high throughput screen utilizing a CCR5 membrane binding assay identifies inhibitors of RANTES binding. This assay utilizes membranes prepared from NIH 3T3 cells expressing the human CCR5 chemokine receptor which have the ability to bind to RANTES, a natural ligand for the receptor. Using a 96-well plate format, membrane preparations are incubated with $^{125}$I-RANTES in the presence or absence of compound for one hour. Compounds are serially diluted over a wide range of 0.001 ug/ml to 1 ug/ml and tested in triplicates. Reaction cocktails are harvested through glass fiber filters, and washed thoroughly. Total counts for replicates are averaged and data reported as the concentration required to inhibit 50 percent of total $^{125}$I-RANTES binding. Compounds with potent activity in the membrane binding assay are further characterized in seconday cell-based HIV-1 entry and replication assays.

HIV-1 Entry Assay

Replication defective HIV-1 reporter virions are generated by cotransfection of a plasmid encoding the NL4-3 strain of HIV-1 (which has been modified by mutation of the envelope gene and introduction of a luciferase reporter plasmid) along with a plasmid encoding one of several HIV-1 envelope genes as described by Connor et al, *Virology*, 206 (1995), p. 935-944. Following transfection of the two plasmids by calcium phosphate precipitation, the viral supernatants are harvested on day 3 and a functional viral titer determined. These stocks are then used to infect U87 cells stably expressing CD4 and the chemokine receptor CCR5 which have been preincubated with or without test compound. Infections are carried out for 2 hours at 37° C., the cells washed and media replaced with fresh media containing compound. The cells are incubated for 3 days, lysed and luciferase activity determined. Results are reported as the concentration of compound required to inhibit 50% of the luciferase activity in the control cultures.

HIV-1 Replication Assay:

This assay uses primary peripheral blood mononuclear cells or the stable U87-CCR5 cell line to determine the effect of anti-CCR5 compounds to block infection of primary HIV-1 strains. The primary lymphocytes are purified from normal healthy donors and stimulated in vitro with PHA and IL-2 three days prior to infection. Using a 96-well plate format, cells are pretreated with drug for 1 hour at 37° C. and subsequently infected with an M-tropic HIV-1 isolates. Following infection, the cells are washed to remove residual inoculum and cultured in the presence of compound for 4 days. Culture supernatants are harvested and viral replication measured by determination of viral p24 antigen concentration.

Calcium Flux Assay:

Cells expressing the HIV coreceptor CCR5 are loaded with calcium sensitive dyes prior to addition of compound or the natural CCR5 ligand. Compounds with agonist properties will induce a calcium flux signal in the cell, while CCR5 antagonists are identified as compounds which do not induce signaling by themselves but are capable of blocking signaling by the natural ligand RANTES.

GTPγS Binding Assay:

A GTPγS binding assay measures receptor activation by CCR5 ligands. This assay measures the binding of $^{35}$S labeled-GTP to receptor coupled G-proteins that occurs as a result of receptor activation by an appropriate ligand. In this assay, the CCR5 ligand, RANTES, is incubated with membranes from CCR5 expressing cells and binding to the receptor activation (or binding) is determined by assaying for bound $^{35}$S label. The assay quantitatively determines if compounds exhibit agonist characteristics by inducing activation of the receptor or alternatively antagonist properties by measuring inhibition of RANTES binding in a competitive or non-competitive fashion.

Chemotaxis Assay:

The chemotaxis assay is a functional assay which characterizes the agonist vs. antagonist properties of the test compounds. The assay measures the ability of a non-adherent murine cell line expressing human CCR5 (BaF-550) to migrate across a membrane in response to either test compounds or natural ligands (i.e., RANTES, MIP-1β). Cells migrate across the permeable membrane towards compounds with agonist activity. Compounds that are antagonists not only fail to induce chemotaxis, but are also capable of inhibiting cell migration in response to known CCR5 ligands.

In the assay to determine inhibition of RANTES binding, compounds of the formulas I-IV range in activity from a Ki of about 0.5 to about 1500 nM, with preferred compounds having a range of activity from about 0.5 to about 750 nM, more preferably about 0.5 to 300 nM, and most preferably about 0.5 to 50 nM.

I claim:

1. A method of treating patients co-infected with [HIV-1] Human Immunodeficiency Virus-1 ("HIV-1") and [HCV] Hepatitis C Virus("HCV") which comprises administering a therapeutically effective amount of pegylated interferon-alfa in association with a therapeutically effective amount of ribavirin and a therapeutically effective amount of [HAART] Highly Active Antiretroviral Therapy and a therapeutically effective amount of a CCR5 antagonist represented by the structural formula I or II or III or IV:

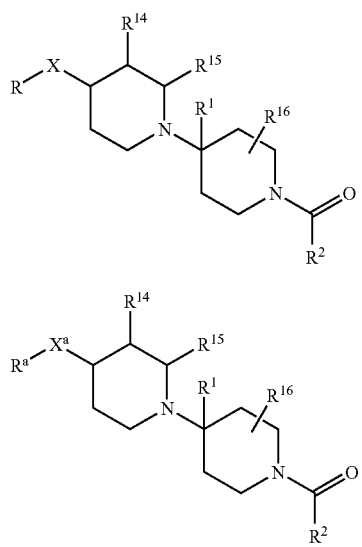

-continued

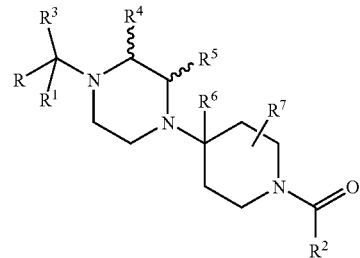

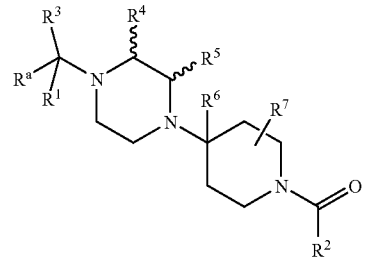

or a pharmaceutically acceptable salt of I or II or II or IV; sufficient to lower HIV-1-RNA and HCV-RNA levels;

wherein in the CCR5 antagonist compounds represented by structural formula I:

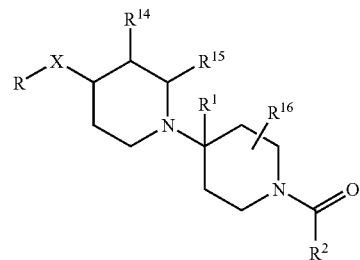

X is —C($R^{13}$)$_2$—, —C($R^{13}$)($R^{19}$)—, —C(O)—, —O—, —NH—, —N(($C_1$-$C_6$)alkyl)-,

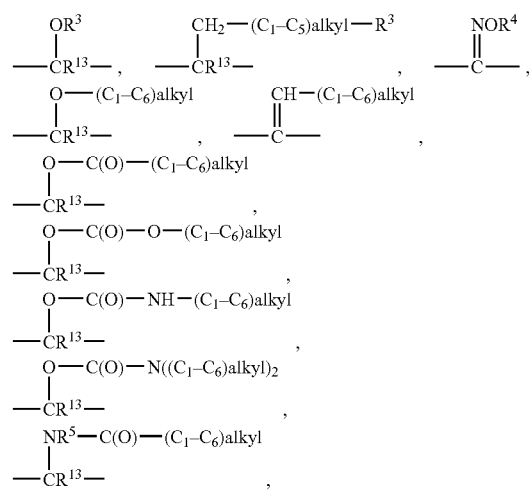

-continued

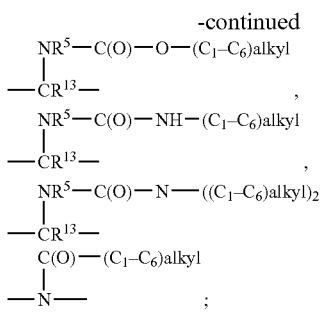

R is $R^6$-phenyl, $R^6$-pyridyl, $R^6$-thiophenyl or $R^6$-naphthyl;

$R^1$ is hydrogen, $(C_1-C_6)$ alkyl or $(C_2-C_6)$alkenyl;

$R^2$ is $R^7$, $R^8$, $R^9$-phenyl; $R^7$, $R^8$, $R^9$-substituted 6-membered heteroaryl;

$R^7$, $R^8$, $R^9$-substituted 6-membered heteroaryl N-oxide;

$R^{10}$, $R^{11}$-substituted 5-membered heteroaryl; naphthyl; fluorenyl; diphenylmethyl

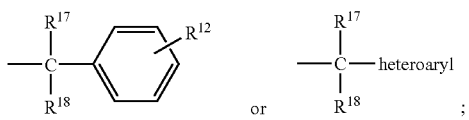

$R^3$ is $R^6$-phenyl, $R^6$-heteroaryl or $R^6$-naphthyl;

$R^4$ is hydrogen, $(C_1-C_6)$ alkyl fluoro-$(C_1-C_6)$ alkyl, cyclopropylmethyl, —$CH_2CH_2OH$, —$CH_2CH_2$—O—$(C_1-C_6)$alkyl, —$CH_2C(O)$—O—$(C_1-C_6)$alkyl, —$CH_2C(O)NH_2$, —$CH_2C(O)$—$NH(C_1-C_6)$alkyl or —$CH_2C(O)$—$N((C_1-C_6)alkyl)_2$;

$R^5$ and $R^{11}$ are independently selected from the group consisting of hydrogen and $(C_1-C_6)$-alkyl;

$R^6$ is 1 to 3 substituents independently selected from the group consisting of hydrogen, halogen, $(C_1-C_6)$ alkyl, $C_1-C_6)$alkoxy, —$CF_3$, $CF_3O$—, $CH_3C(O)$—, —CN, $CH_3SO_2$—, $CF_3SO_2$—, $R^{14}$-phenyl, $R^{14}$-benzyl, $CH_3C(=NOCH_3)$—, $CH_3C(=NOCH_2CH_3)$—,

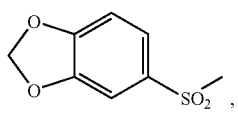

—$NH_2$, —$NHCOCF_3$, —$NHCONH(C_1-C_6$ alkyl), —$NHCO(C_1-C_6$ alkyl), —$NHSO_2(C_1-C_6$ alkyl), 5-membered heteroaryland

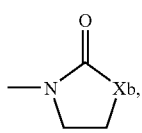

wherein $X^b$ is —O—, —NH—or —$N(CH_3)$—;

$R^7$ and $R^8$ are independently selected from the group consisting of $(C_1-C_6)$alkyl, halogen, —$NR^{20}R^{21}$, —OH, —$CF_3$, —$OCH_3$, —O-acyl, and —$OCF_3$;

$R^9$ is $R^7$, hydrogen, phenyl, —$NO_2$, —CN, —$CH_2F$, —$CHF_2$, —CHO, —CH=$NOR^{20}$, pyridyl, pyridyl N-oxide, pyrimidinyl, pyrazinyl, —$N(R^{20})CONR^{21}R^{22}$, —NHCONH(chloro-$(C_1-C_6)$alkyl), —NHCONH$((C_3-C_{10})$ -cycloalkyl$(C_1-C_6)$alkyl), —NHCO$(C_1-C_6)$alkyl, —$NHCOCF_3$, —$NHSO_2N((C_1-C_6)$alkyl$)_2$, —$NHSO_2(C_1-C_6)$alkyl, —$N(SO_2CF_3)_2$, —$NHCO_2(C_1-C_6)$alkyl, $C_3-C_{10}$ cycloalkyl, —$SR^{23}$, —$SOR^{23}$, —$SO_2R^{23}$, —$SO_2NH(C_1-C_6$ alkyl), —$OSO_2(C_1-C_6)$alkyl, —$OSO_2CF_3$, hydroxy$(C_1-C_6)$alkyl, —$CONR^{20}R^{21}$, —$CON(CH_2CH_2$—O—$CH_3)_2$, —$OCONH(C_1-C_6)$alkyl, —$CO_2R^{20}$, $Si(CH_3)_3$ or —$B(OC(CH_3)_2)_2$;

$R^{10}$ is $(C_1-C_6)$alkyl, —$NH_2$ or $R^{12}$-phenyl;

$R^{12}$ is 1 to 3 substituents independently selected from the group consisting of hydrogen, $(C_1-C_6)$ alkyl, —$CF_3$, —$CO_2R_{20}$, —CN, $(C_1-C_6)$alkoxy and halogen;

$R^{13}$, $R^{14}$, $R^{15}$ and $R^{16}$ are independently selected from the group consisting of hydrogen and $(C_1-C_6)$alkyl;

$R^{17}$ and $R^{18}$ are independently selected from the group consisting of hydrogen and $C_1-C_6$ alkyl, or $R^{17}$ and $R^{18}$ together are a $C_2-C_5$ alkylene group and with the carbon to which they are attached form a Spiro ring of 3 to 6 carbon atoms;

$R^{19}$ is $R^6$-phenyl, $R^6$-heteroaryl, $R^6$-naphthyl, $C_3-C_{10}$ cycloalkyl, $(C_3-C_{10})$cycloalky$(C_1-C_6)$alkyl or $(C_1-C_6)$ alkoxy$(C_1-C_6)$alkyl;

$R^{20}$, $R^{21}$ and $R^{22}$ are independently selected from the group consisting of H and $C_1-C_6$) alkyl; and $R^{23}$ is $C_1-C_6$ alkyl or phenyl;

and wherein in the CCR5 antagonist compounds represented by the structural formula II:

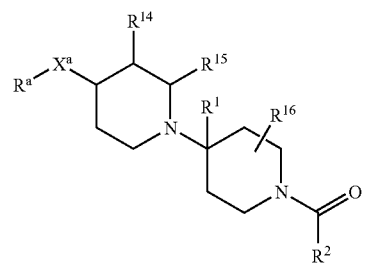

or a pharmaceutically acceptable salt thereof, wherein (1) $X^a$ is —$C(R^{13})_2$—, —$C(R^{13})(R^{19})$—, —C(O)—, —O—, —NH—, —$N((C_1-C_6)$alkyl)—;

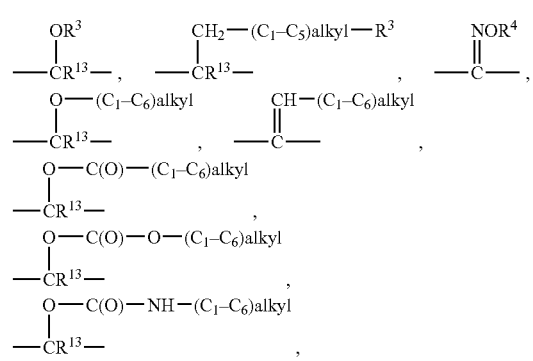

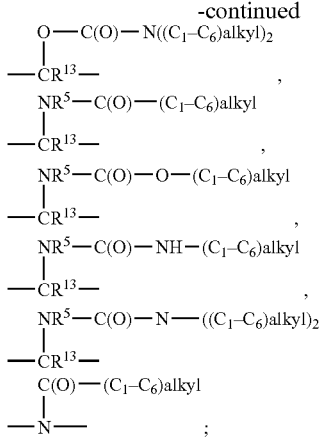

$R^a$ is $R^{6a}$-phenyl, $R^{6a}$-pyridyl, $R^{6a}$-thiophenyl or $R^6$-naphthyl;

$R^1$ is hydrogen, $(C_1$-$C_6)$ alkyl or $(C_2$-$C_6)$ alkenyl;

$R^2$ is $R^7$, $R^8$, $R^9$-phenyl; $R^7$, $R^8$, $R^9$-substituted 6-membered heteroaryl;

$R^7$, $R^8$, $R^9$-substituted 6-membered heteroaryl N-oxide; $R^{10}$, $R^{11}$-substituted 5-membered heteroaryl; naphthyl; fluorenyl; diphenylmethyl

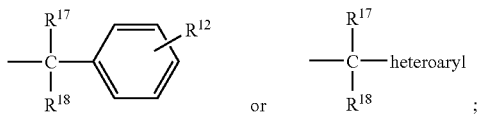

$R^3$ is $R^{10}$-phenyl, pyridyl, pyrimidyl, pyrazinyl or thiazolyl;

$R^4$ is hydrogen, $(C_1$-$C_6)$ alkyl, fluoro-$(C_1$-$C_6)$ alkyl, cyclopropylmethyl, —$CH_2CH_2OH$, —$CH_2CH_2$—O—$(C_1$-$C_6)$alkyl, —$CH_2C(O)$—O—$(C_1$-$C_6)$alkyl, —$CH_2C(O)NH_2$, —$CH_2C(O)$—$NH(C_1$-$C_6)$alkyl or —$CH_2C(O)$—$N((C_1$-$C_6)$alkyl$)_2$;

$R^5$ and $R^{11}$ are independently selected from the group consisting of hydrogen and $(C_1$-$C_6)$-alkyl;

$R^{6a}$ is 1 to 3 substituents independently selected from the group consisting of hydrogen, halogen, —$CF_3$, $CF_3O$—, —CN, —$CF_3SO_2$—, $R^{12}$-phenyl, —NH-COCF$_3$, 5-membered heteroaryl and

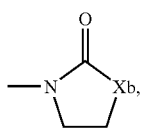

wherein $X^b$ is —O—, —NH— or —N(CH$_3$)—;

$R^6$ is independently selected from the group consisting of $R^{6a}$ and $CH_3SO_2$—;

$R^7$ and $R^8$ are independently selected from the group consisting of $(C_1$-$C_6)$alkyl, halogen, —$NR^{20}R^{21}$, —OH, —$CF_3$, —$OCH_3$, —O—acyl, and —$OCF_3$;

$R^9$ is $R^7$, hydrogen, phenyl, —$NO_2$, —CN, —$CH_2F$, —$CHF_2$, —CHO, —CH=NOR$^{20}$, pyridyl, pyridyl N-oxide, pyrimidinyl, pyrazinyl, —N(R$^{20}$)CONR$^{21}$R$^{22}$, —NHCONH(chloro-$(C_1$-$C_6)$alkyl), —NHCONH($(C_3$-$C_{10})$-cycloalkyl$(C_1$-$C_6)$alkyl), —NHCO($C_1$-$C_6)$alkyl, —NHCOCF$_3$, —NHSO$_2$N$((C_1$-$C_6)$alkyl$)_2$, —NHSO$_2(C_1$-$C_6)$alkyl, —N(SO$_2$CF$_3)_2$, —NHCO$_2(C_1$-$C_6)$alkyl, $C_3$-$C_{10}$ cycloalkyl, —SR$^{23}$, —SOR$^{23}$, —SO$_2$R$^{23}$, —SO$_2$NH$(C_{1}$-$_6$ alkyl), —OSO$_2(C_1$-$C_6)$alkyl, —OSO$_2$CF$_3$, hydroxy$(C_1$-$C_6)$ alkyl, —CON R$^{20}$R$^{21}$, —CON(CH$_2$CH$_2$—O—CH$_3)_2$, —OCONH$(C_1$-$C_6)$alkyl, —CO$_2$R$^{20}$, —Si(CH$_3)_3$ or —B(OC(CH$_3)_2)_2$;

$R^{10}$ is $(C_1$-$C_6)$alkyl, —NH$_2$ or $R^{12}$-phenyl;

$R^{12}$ is 1 to 3 substituents independently selected from the group consisting of hydrogen, $(C_1$-$C_6)$ alkyl, —$CF_3$, —$CO_2R_{20}$, —CN, $(C_1$-$C_6)$alkoxy and halogen;

$R^{13}$, $R^{14}$, $R^{15}$ and $R^{16}$ are independently selected from the group consisting of hydrogen and $(C_1$-$C_6)$alkyl;

$R^{17}$ and $R^{18}$ are independently selected from the group consisting of hydrogen and $(C_1$-$C_6)$ alkyl, or $R^{17}$ and $R^{18}$ together are a $C_2$-$C_5$ alkylene group and with the carbon to which they are attached form a spiro ring of 3 to 6 carbon atoms;

$R^{19}$ is $R^6$-phenyl, $R^6$-heteroaryl, $R^6$-naphthyl, $C_3$-$C_{10}$ cycloalkyl, $(C_3$-$C_{10})$cycloalkyl$(C_1$-$C_6)$alkyl or $(C_1$-$C_6)$ alkoxy$(C_1$-$C_6)$alkyl;

$R^{20}$, $R^{21}$ and $R^{22}$ are independently selected from the group consisting of H and $C_1$-$C_6)$ alkyl; and $R^{23}$ is $C_1$-$C_6$ alkyl or phenyl; or (2):

$X^a$ is —C(R$^{13})$(R$^{19})$—, —C(O)—, —O—, —NH—, —N($(C_1$-$C_6)$alkyl)—,

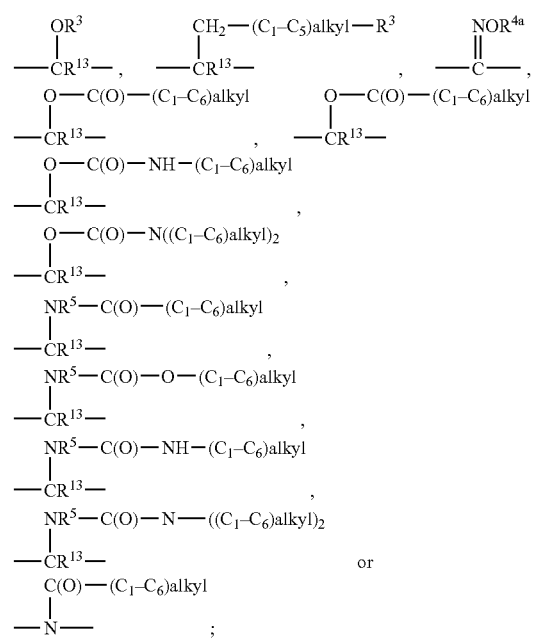

$R^a$ is $R^{6b}$-phenyl, $R^{6b}$-pyridyl or $R^{6b}$-thiophenyl;

$R^{4a}$ is fluoro-$C_1$-$C_6$ alkyl, cyclopropylmethyl, —$CH_2CH_2OH$, —$CH_2CH_2$—O—$(C_1$-$C_6)$alkyl, —$CH_2C(O)$—O—$(C_1$-$C_6)$alkyl, —$CH_2C(O)NH_2$, —$CH_2C(O)$—$NH$—$(C_1$-$C_6)$alkyl or —$CH_2C(O)$—N$((C_1$-$C_6)$alkyl$)_2$;

$R^{6b}$ is $CH_3SO_2$—; and $R^1$, $R^2$, $R^3$, $R^5$, $R^{14}$, $R^{15}$, $R^{16}$ and $R^{19}$ are as defined in II(1);

and wherein in the CCR5 antagonist compounds represented by the structural formula III:

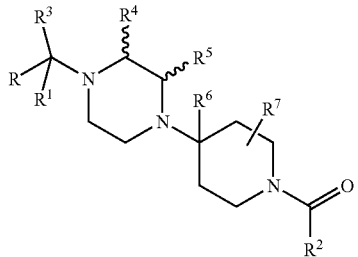

R is $R^8$-phenyl, $R^8$-pyridyl, $R^8$-thiophenyl or $R^8$-naphthyl;

$R^1$ is hydrogen or $C_1$-$C_6$ alkyl;

$R^2$ is $R^9$, $R^{10}$, $R^{11}$-phenyl; $R^9$, $R^{10}$, $R^{11}$-substituted 6-membered heteroaryl; $R^9$, $R^{10}$, $R^{11}$-substituted 6-membered heteroaryl N-oxide; $R^{12}$, $R^{13}$-substituted 5-membered heteroaryl; naphthyl; fluorenyl; diphenylmethyl

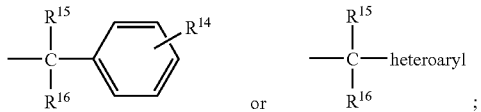

$R^3$ is hydrogen, $C_1$-$C_6$ alkyl, ($C_1$-$C_6$)alkoxy($C_1$-$C_6$)alkyl, $C_3$-$C_{10}$ cycloalkyl, $C_3$-$C_{10}$ cycloalkyl($C_1$-$C_6$)alkyl, $R^8$-phenyl, $R^8$-phenyl($C_1$-$C_6$)alkyl, $R^8$-naphthyl, $R^8$-naphthyl($C_1$-$C_6$)alkyl, $R^8$-heteroaryl or $R^8$-heteroaryl($C_1$-$C_6$)alkyl;

$R^4$, $R^5$, $R^7$ and $R^{13}$ are independently selected from the group consisting of hydrogen and ($C_1$-$C_6$)-alkyl;

$R^6$ is hydrogen, $C_1$-$C_6$ alkyl or ($C_2$-$C_6$)alkenyl;

$R^8$ is 1 to 3 substituents independently selected from the group consisting of hydrogen, halogen, ($C_1$-$C_6$) alkyl, $C_1$-$C_6$ alkoxy, —$CF_3$, $CF_3O$—, $CH_3C(O)$—, —CN, $CH_3SO_2$—, $CF_3SO_2$—, $R^{14}$-phenyl, $R^{14}$-benzyl, $CH_3C(=NOCH_3)$, $CH_3C(=NOCH_2CH_3)$,

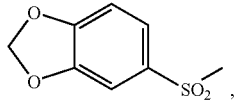

—$NH_2$, —$NHCOCF_3$, —$NHCONH(C_1$-$C_6$ alkyl), —NHCO($C_1$-$C_6$ alkyl), —$NHSO_2(C_1$-$C_6$ alkyl), 5-membered heteroaryl and

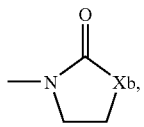

wherein $X^b$ is —O—, —NH— or —N($CH_3$)—;

$R^9$ and $R^{10}$ are independently selected from the group consisting of ($C_1$-$C_6$)alkyl, halogen, —$NR^{17}R^{18}$, —OH, —$CF_3$, $OCH_3$, —O—acyl, —$OCF_3$ and —Si($CH_3$)$_3$;

$R^{11}$ is $R^9$, hydrogen, phenyl, —$NO_2$, —CN, —$CH_2F$, —$CHF_2$, —CHO, —CH=$NOR^{17}$, pyridyl, pyridyl N-oxide, pyrimidinyl, pyrazinyl, —N($R^{17}$)$CONR^{18}R^{19}$, —NHCONH(chloro-($C_1$-$C_6$)alkyl), —NHCONH(($C_3$-$C_1$)cycloalkyl($C_{1-6}$)alkyl), —NHCO ($C_1$-$C_6$)alkyl, —$NHCOCF_3$, —$NHSO_2N((C_1$-$C_6$) alkyl)$_2$, —$NHSO_2(C_1$-$C_6$)alkyl, —$N(SO_2CF_3)_2$, —$NHCO_2(C_1$-$C_6$)alkyl, $C_3$-$C_{10}$ cycloalkyl, —$SR^{20}$, —$SOR^{20}$, —$SO_2R^{20}$, —$SO_2NH(C_1$-$C_6$ alkyl), —$OSO_2$($C_1$-$C_6$)alkyl, —$OSO_2CF_3$, hydroxy($C_1$-$C_6$)alkyl, —CON $R^{17}R^{18}$, —CON($CH_2CH_2$—O—$CH_3$)$_2$, —OCONH($C_1$-$C_6$)alkyl, —$CO_2R^{17}$, —Si($CH_3$)$_3$ or —B(OC($CH_3$)$_2$)$_2$;

$R^{12}$ is ($C_1$-$C_6$)alkyl, —$NH_2$ or $R^{14}$-phenyl;

$R^{14}$ is 1 to 3 substituents independently selected from the group consisting of hydrogen, ($C_1$-$C_6$) alkyl, —$CF_3$, —$CO_2R_{17}$, —CN, ($C_1$-$C_6$)alkoxy and halogen;

$R^{15}$ and $R^{16}$ are independently selected from the group consisting of hydrogen and $C_1$-$C_6$) alkyl, or $R^{15}$ and $R^{16}$ together are a $C_2$-$C_5$ alkylene group and with the carbon to which they are attached form a spiro ring of 3 to 6 carbon atoms;

$R^{17}$, $R^{18}$ and $R^{19}$ are independently selected from the group consisting of H and ($C_1$-$C_6$) alkyl; and $R^{20}$ is ($C_1$-$C_6$) alkyl or phenyl;

and wherein in the CCR5 antagonist compounds represented by the structural formula IV:

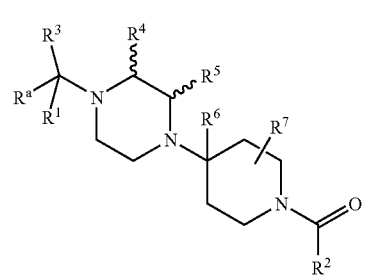

or a pharmaceutically acceptable salt thereof, wherein (1) $R^a$ is $R^{8a}$-phenyl, $R^{8b}$-pyridyl, $R^{8b}$-thiophenyl or $R^8$-naphthyl;

$R^1$ is hydrogen or ($C_1$-$C_6$) alkyl;

$R^2$ is $R^9$, $R^{10}$, $R^{11}$-phenyl; $R^9$, $R^{10}$, $R^{11}$-substituted 6-membered heteroaryl; $R^9$, $R^{10}$, $R^{11}$-substituted 6-membered heteroaryl N-oxide;

$R^{12}$, $R^{13}$-substituted 5-membered heteroaryl; naphthyl; fluorenyl; diphenylmethyl,

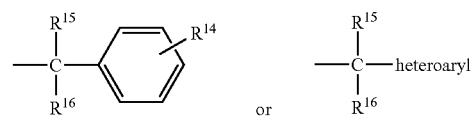

$R^3$ is hydrogen, ($C_1$-$C_6$) alkyl, ($C_1$-$C_6$)alkoxy($C_1$-$C_6$) alkyl, $C_3$-$C_{10}$ cycloalkyl, $C_3$-$C_{10}$ cycloalkyl($C_1$-$C_6$) alkyl, $R^8$-phenyl, $R^8$-phenyl($C_1$-$C_6$)alkyl, $R^8$-naphthyl, $R^8$naphthyl($C_1$-$C_6$)alkyl, $R^8$-heteroaryl or $R^8$-heteroaryl($C_1$-$C_6$)alkyl;

$R^4$, $R^5$, $R^7$ and $R^{13}$ are independently selected from the group consisting of hydrogen and ($C_1$-$C_6$)-alkyl;

$R^6$ is hydrogen, ($C_1$-$C_6$) alkyl or ($C_2$-$C_6$)alkenyl;

$R^8$ is 1 to 3 substituents independently selected from the group consisting of hydrogen, halogen, $C_1$-$C_6$) alkyl, $C_1$-$C_6$ alkoxy, —$CF_3$, $CF_3O$—, $CH_3C(O)$—, —CN, $CH_3SO_2$—, $CF_3SO_2$—, $R^{14}$-phenyl, $R^{14}$-benzyl, $CH_3C(=NOOH_3)$, $CH_3C(=NOCH_2CH_3)$,

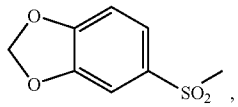

—NH$_2$, —NHCOOF$_3$, —NHCONH(C$_1$-C$_6$ alkyl), —NHCO(C$_1$-C$_6$ alkyl), —NHSO$_2$(C$_1$-C$_6$ alkyl), 5-membered heteroaryl and

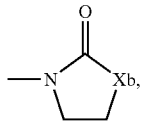

wherein X$^b$ is —O—, —NH— or —N(CH$_3$)—;

R$^{8a}$ is 1 to 3 substituents independently selected from the group consisting of hydrogen, halogen, —CF$_3$, CF$_3$O—, —CN, CF$_3$SO$_2$—, R$^{14}$-phenyl, —NHCOCF$_3$, 5-membered heteroaryl and

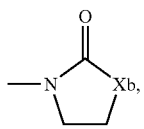

wherein X$^b$ is as defined above;

R$^{8b}$ is 1 to 3 substituents independently selected from the group consisting of hydrogen, halogen, —CF$_3$, CF$_3$O—, CH$_3$C(O)—, —CN, CF$_3$SO$_2$—, R$^{14}$-benzyl, CH$_3$C(=NOCH$_3$), CH$_3$C(=NOCH$_2$CH$_3$),

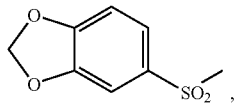

—NHCOCF$_3$, 5-membered heteroaryl and

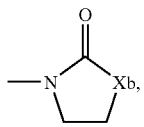

wherein X$^b$ is as defined above;

R$^9$ and R$^{10}$ are independently selected from the group consisting of (C$_1$-C$_6$)alkyl, halogen, —NR$^{17}$R$^{18}$, —OH, —CF$_3$, —OCH$_3$, —O-acyl, —OCF$_3$ and —Si(CH$_3$)$_3$;

R$^{11}$ is R$^9$, hydrogen, phenyl, —NO$_2$, —CN, —CH$_2$F, —CHF$_2$, —CHO, —CH=NOR$^{17}$, pyridyl, pyridyl N-oxide, pyrimidinyl, pyrazinyl, —N(R$^{17}$)CONR$^{18}$R$^{19}$, —NHCONH(chloro-(C$_1$-C$_6$)alkyl), —NHCONH((C$_3$-C$_1$)cycloalkyl(C$_1$-C$_6$)alkyl), —NHCO(C$_1$-C$_6$)alkyl, —NHCOCF$_3$, —NHSO$_2$N((C$_1$-C$_6$)alkyl)$_2$, —NHSO$_2$(C$_1$-C$_6$)alkyl, —N(SO$_2$CF$_3$)$_2$, —NHCO$_2$(C$_1$-C$_6$)alkyl, C$_3$-C$_{10}$ cycloalkyl, —SR$^{20}$, —SOR$^{20}$, SO$_2$R$^{20}$, —SO$_2$NH(C$_1$-C$_6$ alkyl), —OSO$_2$(C$_1$-C$_6$)alkyl, —OSO$_2$CF$_3$, hydroxy(C$_1$-C$_6$)alkyl, —CON R$^{17}$R$^{18}$, —CON(CH$_2$CH$_2$—O—CH$_3$)$_2$, —OCONH(C$_1$-C$_6$)alkyl, —CO$_2$R$^{17}$, —Si(CH$_3$)$_3$ or —B(OC(CH$_3$)$_2$)$_2$;

R$^{12}$ is (C$_1$-C$_6$)alkyl, —NH$_2$ or R$^{14}$-phenyl;

R$^{14}$ is 1 to 3 substituents independently selected from the group consisting of hydrogen, (C$_1$-C$_6$) alkyl, —CF$_3$, —CO$_2$R$_{17}$, —CN, (C$_1$-C$_6$)alkoxy and halogen;

R$^{15}$ and R$^{16}$ are independently selected from the group consisting of hydrogen and C$_1$-C$_6$ alkyl, or R$^{15}$ and R$^{16}$ together are a C$_2$-C$_5$ alkylene group and with the carbon to which they are attached form a spiro ring of 3 to 6 carbon atoms;

R$^{17}$, R$^{18}$ and R$^{19}$ are independently selected from the group consisting of H and C$_1$-C$_6$ alkyl; and R$^{20}$ is (C$_1$-C$_6$) alkyl or phenyl; or (2) R$^a$ is R$^8$-phenyl, R$^8$-pyridyl or R$^8$-thiophenyl;

R$^2$ is fluorenyl, diphenylmethyl,

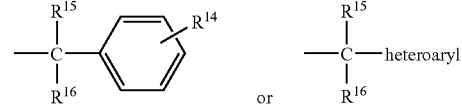

and R$^1$, R$^3$, R$^4$, R$^5$, R$^6$, R$^7$, R$^8$, R$^9$, R$^{10}$, R$^{11}$, R$^{12}$, R$^{13}$, R$^{14}$, R$^{15}$, R$^{16}$, R$^{17}$, R$^{18}$, R$^{19}$ and R$^{20}$ are as defined in IV(1).

2. The method of claim 1, wherein the patients are treatment-naive patients.

3. The method of claim 1, wherein the patients are treatment-experienced patients.

4. The method of claim 1, wherein the pegylated interferon-alfa administered is a pegylated interferon alfa-2b and wherein the amount of pegylated interferon alfa-2b administered is in the range of about 0.5 to about 3.0 micrograms per kilogram in a single dose QW or divided doses BIW.

5. The method of claim 1, wherein the pegylated interferon-alfa administered is a pegylated interferon alfa-2b and wherein the amount of pegylated interferon alfa-2b administered is in the range of about 0.75 to about 1.5 micrograms per kilogram in a single dose QW or divided doses BIW.

6. The method of claim 1, wherein the pegylated interferon-alfa administered is a pegylated interferon alfa-2b and wherein the amount of pegylated interferon alfa-2b administered is in the range of about 0.5 to about 3.0 micrograms per kilogram in a single dose QW.

7. The method of claim 1, wherein the pegylated interferon-alfa administered is a pegylated interferon alfa-2b and wherein the amount of pegylated interferon alfa-2b administered is in the range of about 0.25 to about 1.5 micrograms per kilogram BIW.

8. The method of claim 1, wherein the pegylated interferon-alfa administered is a pegylated interferon alfa-2b and wherein the amount of pegylated interferon alfa-2b administered is in the range of about 0.75 to about 1.5 micrograms per kilogram in a single dose QW.

9. The method of claim 1, wherein the pegylated interferon-alfa administered is a pegylated interferon alfa-2b and wherein the amount of pegylated interferon alfa-2b administered is about 1.5 micrograms per kilogram in a single dose QW.

10. The method of claim 1, wherein the pegylated interferon-alfa administered is a pegylated interferon alfa-2b and wherein the amount of pegylated interferon alfa-2b administered is in the range of about 0.375 to about 1.5 micrograms per kilogram BIW.

* * * * *